US011007364B2

(12) United States Patent
Carroll

(10) Patent No.: US 11,007,364 B2
(45) Date of Patent: May 18, 2021

(54) SPINAL CORD STIMULATION WITH INTERFERENTIAL CURRENT

(71) Applicant: Meagan Medical, Inc., Vancouver, WA (US)

(72) Inventor: William J. Carroll, LaCenter, WA (US)

(73) Assignee: Meagan Medical, Inc., Vancouver, WA (US)

(*) Notice: Subject to any disclaimer, the term of this patent is extended or adjusted under 35 U.S.C. 154(b) by 167 days.

(21) Appl. No.: 16/406,204

(22) Filed: May 8, 2019

(65) Prior Publication Data

US 2019/0262616 A1 Aug. 29, 2019

Related U.S. Application Data

(63) Continuation of application No. 15/456,730, filed on Mar. 13, 2017, now Pat. No. 10,350,414, which is a
(Continued)

(51) Int. Cl.
*A61N 1/36* (2006.01)
*A61N 1/05* (2006.01)
(Continued)

(52) U.S. Cl.
CPC ......... *A61N 1/0553* (2013.01); *A61N 1/0551* (2013.01); *A61N 1/06* (2013.01);
(Continued)

(58) Field of Classification Search
None
See application file for complete search history.

(56) References Cited

U.S. PATENT DOCUMENTS 3,096,768 A 7/1963 Griffith, Jr.
3,822,708 A 7/1974 Zilber
(Continued)

FOREIGN PATENT DOCUMENTS

CN 1138829 12/1996
CN 104117146 10/2014
(Continued)

OTHER PUBLICATIONS

Kalliomäki, J., Granmo, M., Schouenborg, J., "Spinal NMDA-receptor dependent amplification of nociceptive transmission to rat primary somatosensory cortex (SI)", Pain., Jul. 2003;104(1-2):195-200.
(Continued)

*Primary Examiner* — Erica S Lee
(74) *Attorney, Agent, or Firm* — McDonnell Boehnen Hulbert & Berghoff LLP

(57) ABSTRACT

A stimulator and a method using electrical stimulation of a spinal cord, for providing positive regulation of multiple symptoms other than pain is disclosed. An example method includes positioning a first pair of implantable electrodes to a dura matter in an epidural space proximate to a subject's spinal cord at predetermined locations, positioning a second pair of implantable electrodes to the dura matter in the epidural space proximate to the subject's spinal cord at predetermined locations, and transmitting signals of first and second frequencies through the first and second pairs of implantable electrodes respectively, so that the signals of the first and second frequencies interfere with each other to produce at least one beat signal proximate to the subject's spinal cord. The at least one beat signal has a frequency within a range of more than 250 Hz to about 15,000 Hz.

20 Claims, 15 Drawing Sheets

Related U.S. Application Data continuation of application No. 14/820,192, filed on Aug. 6, 2015, now Pat. No. 9,630,012.

(51) Int. Cl.
  *A61N 1/06* (2006.01)
  *A61N 1/32* (2006.01)

(52) U.S. Cl.
  CPC ........... *A61N 1/323* (2013.01); *A61N 1/3616* (2013.01); *A61N 1/36062* (2017.08); *A61N 1/36071* (2013.01); *A61N 1/36125* (2013.01); *A61N 1/36171* (2013.01); *A61N 1/36182* (2013.01); *A61N 1/0558* (2013.01)

(56) References Cited

U.S. PATENT DOCUMENTS

| | | |
|---|---|---|
| 4,153,061 A | 5/1979 | Nemec |
| 4,374,524 A | 2/1983 | Hudek et al. |
| 4,598,713 A | 7/1986 | Hansjurgens et al. |
| 4,848,347 A | 7/1989 | Hall |
| 5,002,053 A | 3/1991 | Garcia-Rill et al. |
| 5,107,835 A | 4/1992 | Thomas |
| 5,161,530 A | 11/1992 | Gamble |
| 5,215,086 A | 6/1993 | Terry et al. |
| 5,269,304 A | 12/1993 | Matthews |
| 5,411,535 A | 5/1995 | Fujii et al. |
| 5,443,486 A | 8/1995 | Hrdicka et al. |
| 5,466,247 A | 11/1995 | Scheiner et al. |
| 5,512,057 A | 4/1996 | Reiss et al. |
| 5,643,330 A | 7/1997 | Holsheimer et al. |
| 5,776,173 A | 7/1998 | Madsen et al. |
| 6,052,624 A | 4/2000 | Mann |
| 6,233,488 B1 | 5/2001 | Hess |
| 6,505,078 B1 | 1/2003 | King et al. |
| 6,871,099 B1 | 3/2005 | Whitehurst et al. |
| 7,349,743 B2 | 3/2008 | Tadlock |
| 8,977,363 B2 | 3/2015 | Carroll et al. |
| 9,630,012 B2 | 4/2017 | Carroll |
| 2001/0031999 A1 | 10/2001 | Carter et al. |
| 2002/0099425 A1 | 7/2002 | Johnson et al. |
| 2004/0167584 A1 | 8/2004 | Carroll et al. |
| 2004/0267333 A1 | 12/2004 | Kronberg |
| 2007/0185541 A1 | 8/2007 | DiUbaldi et al. |
| 2010/0114260 A1 | 5/2010 | Donofrio |
| 2010/0152817 A1 | 6/2010 | Gillbe |
| 2013/0165829 A1 | 6/2013 | Carroll |
| 2013/0282070 A1 | 10/2013 | Cowan et al. |
| 2014/0121728 A1 | 5/2014 | Dhillon et al. |
| 2014/0249466 A1* | 9/2014 | Hakim ............... A61F 7/02 604/20 |
| 2015/0142077 A1 | 5/2015 | Caroll |
| 2017/0036029 A1 | 2/2017 | Carroll |
| 2017/0182324 A1 | 6/2017 | Carroll |

FOREIGN PATENT DOCUMENTS

| | | |
|---|---|---|
| CN | 104203338 | 12/2014 |
| CN | 104619379 | 5/2015 |
| JP | 2014-514069 | 6/2014 |
| JP | 2015-57256 | 3/2015 |
| WO | WO 2012/138782 | 10/2012 |
| WO | WO 2012/172545 | 12/2012 |

OTHER PUBLICATIONS

Mediratta and Nicoll, "Conduction velocities of corticospinal axons in the rate studied by recording cortical antidromic responses", J Physiol., Mar. 1983; 336:545-61.

Stewart et al., "Corticospinal responses to electrical stimulation of motor cortex in the rat", Brain Research, Feb. 5, 1990;508(2):341-4.

Chapman and Yeomans, "Motor cortex and pyramidal tract axons responsible for electrically evoked forelimb flexion: refractory periods and conduction velocities", Neuroscience 1994; 59(3):699-711.

Cheing, et al., "Analgesic effects of transcutaneous electrical nerve stimulation and interferential currents on heat pain in healthy subjects", J. Rehabil Med., 2003; 35:15-19.

Kamondetdacha et al., "Calculations of induced current distribution in a human model from low frequency electrodes" School of Electrical and Computer Engineering, Purdue University, Jul. 26, 2005; 1-33.

Holsheimer et al., "Effectiveness of spinal cord stimulation in the management of chronic pain: analysis of technical drawbacks and solutions", Neurosurgery: vol. 40(5) May 1997; 990-99.

Holsheimer, "Which Neuronal Elements are Activated Directly by Spinal Cord Stimulation", Institute for Biomedical Technology, University of Twente, pp. 24-31.

DeDominico, "Technical Aspects of Interferential Currents", New Dimensions in Interferential Therapy a Theoretical and Clinical Guide, Apr. 1987, chapter 2, 12-16.

Barolat et al., "Multifactorial Analysis of Epidural Spinal Cord Stimulation", Sterotact Funct Neurosurg, No. 56, pp., 1991, 77-103.

Vogel et al., "Long-term Effects of Spinal Cord Stimulation in Chronic Pain Syndrome", Journal of Neurology, vol. 233, 1986, pp. 16-18.

Donner et al., "Long-Term Effects of Nerve Blocks in Chronic Pain", Current Opinions in Anesthesiology, Oct. 1998, vol. 11, No. 5, pp. 523-532.

North et al., "Spinal Cord Stimulation for Chronic Parts of Spinal Origin", SPINE, 2002, col. 27, No. 22, pp. 2584-2591.

Taylor et al, "Spianl Cord Stimulation for Chronic Back and Leg Pain and Failed Back Surgery Syndrome: A Systematic Review and Analysis of Prognostic Factors", SPINE, 2004, col. 30, No. 1, pp. 152-160.

Carter, "Spinal Cord Stimulation in Chronic Pain: A Review of Evidence" Anaesth Intensive Care, 2004, vol. 32, No. 1, pp. 11-21.

Kumar et al., "Spinal Cord Stimulation versus Conventional Medical Management for Neuropathic Pain: A Multicentre Randomised Controlled Trial in Patients with Failed Back Surgery Syndrome", Pain 132, 2007, pp. 187-188.

"Editorial", Robert Foreman, Department of Physiology, University of Oklahoma Health Science Center, Oklahoma City, OK, pp. 1-3.

Ascending Sensory Pathways, Chapter 10, pp. 137-170, retrieved from the internet: http://www.blackwellpublishing.com/patestas/chapters/10.pdf on Aug. 6, 2015.

Bel et al., "Dorsal column stimulation: cost to benefit analysis"; Acta Neurochir Suppl (Wien), 52(): 121-3, 1991.

International Search Report and Written Opinion prepared by the US Patent Office in International Application No. PCT/US2016/45131 dated Sep. 16, 2016.

Official Action issued by the Canadian Patent Office in application No. 2,993,814 dated Aug. 25, 2020.

First Office Action issued by the Chinese Patent Office in application No. 201680051855.4 dated Sep. 29, 2020.

* cited by examiner

SPINAL CORD STIMULATION WITH INTERFERENTIAL CURRENT

CROSS REFERENCE TO RELATED PATENT APPLICATIONS

The present disclosure is a continuation of U.S. patent application Ser. No. 15/456,730, filed on Mar. 13, 2017, which is a continuation of U.S. patent application Ser. No. 14/820,192, filed on Aug. 6, 2015, the entire disclosures of each of which are herein incorporated by reference.

FIELD

The present disclosure is generally related to spinal cord stimulation and, more particularly, is related to an apparatus and method for the electrical stimulation of the spinal cord using an interferential current pattern for treating chronic pain conditions.

BACKGROUND

Electrical stimulation of the posterior spinal cord, spinal cord stimulation (SCS), has developed into an effective therapeutic tool for treating chronic pain conditions. However, very little is known about the sites of activation or the neural mechanisms evoked by SCS that relieve pain and promote changes in the function of somatic and visceral structures.

Spinal Cord Stimulation is most commonly used for patients with chronic intractable pain syndromes. It has also been useful for treating movement disorders and is occasionally used following head injuries. However, one complication with SCS is that of accommodation or habituation to the stimulation signal. Companies that manufacture spinal stimulation devices have developed complex stimulation programs and devoted chapters on techniques to reduce the problem of accommodation during SCS (Alfano S, Darwin J, Picullel B: Spinal Cord Stimulation, Patient Management Guidelines for Clinicians, Medtronic, Inc.). Accommodation is when the body habituates or becomes accustomed to an activity or signal and then starts to ignore or 'tune it out'. By varying the signal or keeping the focal point of the signal moving, accommodation can be minimized.

Dorsal Column Stimulation (DCS) or SCS using an electrical current pattern has shown to be a cost benefit in treating chronic pain disorders in patients (Dorsal column stimulation: cost to benefit analysis; *Acta Neurochir Suppl* (Wien), 52( ): 121-3, 1991).

SCS stimulates the dorsal column in a somewhat superficial manner as pointed out by Holsheimer (Holsheimer J: Which Neuronal Elements are activated Directly by Spinal Cord Stimulation, *Neuromodulation*, Volume 5, Number 1: 25-31, 2002). The electrodes are normally attached to the dura matter in the epidural space, and most of the current distribution remains in the cerebrospinal fluid (CSF) and does not project deeply into the dorsal column.

Thus, traditional SCS stimulation has limited application because of the spread of the stimulating electrical field within the CSF as intensity of stimulation increases. This is due to the highly conductive nature of the CSF as compared to the less conductive nature of the spinal cord tissue itself. Thus, traditional SCS stimulation is "amplitude limited" to a relatively narrow surface area of the spinal cord. Frequently, patient satisfaction with electrical stimulation is compromised by the recruitment of adjacent neuronal structures that, when activated, can create discomfort, motor contractions, and outright pain. The efficacy of the therapy is thus limited.

Thus, a heretofore unaddressed need exists in the industry to address the aforementioned deficiencies and inadequacies with regard to accommodation or habituation to the spinal cord stimulation signal when used in the treatment of chronic pain syndromes.

SUMMARY

Within examples, using interferential stimulation with implantable leads to decrease the problem of accommodation might prove to be advantageous. Providing an interferential component to the electrode array of the SCS allows the crossing of the two signals or overlap of two signals, and the resultant additive effect of the beat frequency produces deeper penetration of the signal and a higher resultant amplitude at the stimulation site. The interferential current would recruit larger numbers of dorsal column fibers and provide greater levels of pain relief and benefit to intractable pain patients.

Within examples, a method for spinal cord stimulation treatment using electrical stimulation of a spinal cord is described. The method comprises positioning a first pair of implantable electrodes to a dura matter in an epidural space proximate to a subject's spinal cord at predetermined locations, positioning a second pair of implantable electrodes to the dura matter in the epidural space proximate to the subject's spinal cord at predetermined locations, and transmitting signals of first and second frequencies through the first and second pairs of implantable electrodes respectively, so that the signals of the first and second frequencies interfere with each other to produce at least one beat signal proximate to the subject's spinal cord. The at least one beat signal has a frequency within a range of more than 250 Hz to about 15,000 Hz.

Within other examples, an electrical stimulator for spinal cord treatment is described. The stimulator comprises an interferential current generator that generates an interferential output including first and second signals having different first and second frequencies, and at least two pairs of implantable electrodes having first and second ends. The first ends are connected to the interferential current generator and the second ends are configured to be implanted to a dura matter in an epidural space at predetermined locations proximate to a subject's spinal cord. Each of the at least two pairs of implantable electrodes carries one of the first and second signals such that the first and second frequencies interfere with each other to produce at least one beat signal proximate to the subject's spinal cord, and the at least one beat signal has a frequency within a range of more than 250 Hz to about 15,000 Hz.

These as well as other aspects, advantages, and alternatives will become apparent to those of ordinary skill in the art by reading the following detailed description, with reference where appropriate to the accompanying drawings.

BRIEF DESCRIPTION OF THE DRAWINGS

Many aspects of the disclosure can be understood with reference to the following drawings. The components in the drawings are not necessarily to scale. Moreover, in the drawings, like reference numerals designate corresponding parts throughout the several views.

DETAILED DESCRIPTION

Figure 1:
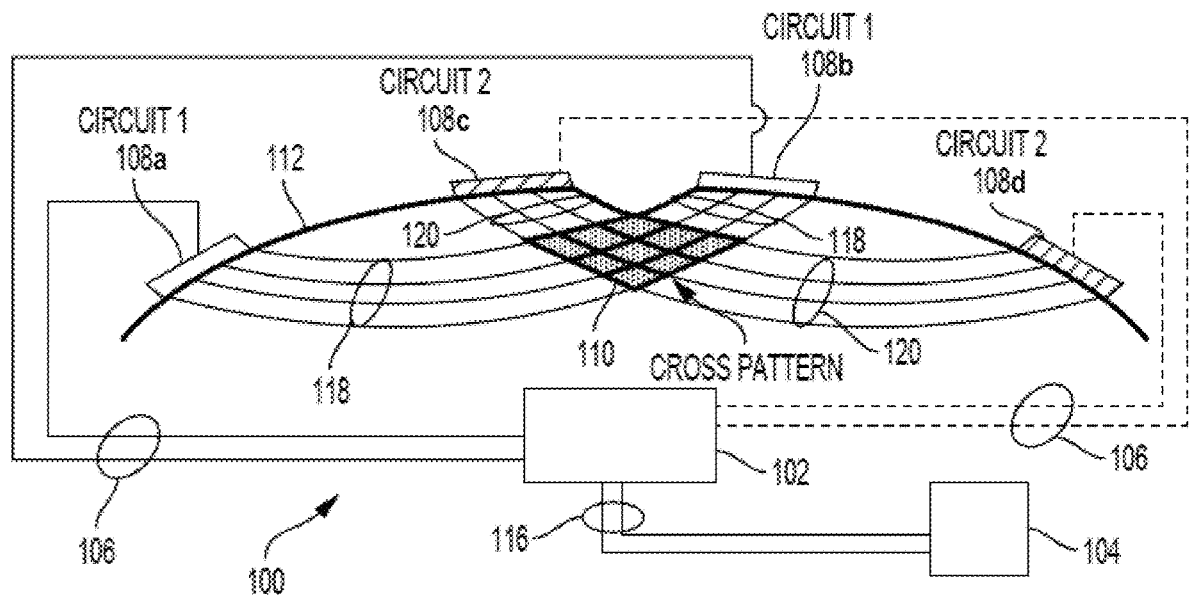
FIG. 1 is a perspective view of an interferential current set up by two circuits that are arranged in a cross pattern, according to an example embodiment.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Embodiments of the present disclosure provide an apparatus and method for the treatment of chronic pain syndromes using electrical stimulation of the spinal cord. Within examples, an electrical stimulator is provided for the treatment of intractable pain syndromes that includes implantable electrodes implanted to a dura mater proximate to a subject's spinal cord, and interferential stimulation is used to produce a beat frequency signal such that a majority of the beat frequency signal is directionally distributed and controlled to avoid stimulating adjacent and/or inappropriate neuronal targets within the spinal canal, thereby creating a far more efficacious neuro-stimulation field in the treatment of pain. In other examples, a majority of the beat frequency signal is directionally distributed and controlled to avoid remaining in and shunting through the cerebrospinal fluid proximate to the subject's spinal cord.

An effective area of stimulation is controlled by the quantity of electrodes, positioning of the electrodes and electrode cross or interference pattern orientation. Thus, the beat frequency signal can be directionally controlled.

Within examples, the apparatus utilizes an interferential current that has a base medium frequency alternating current between about 500 Hz and about 20 KHz. An interferential current is set up between two circuits that are arranged in a cross-pattern or in a parallel pattern on the subject's targeted area of stimulation. Where the circuits superimpose in a cross-pattern, the resultant beat frequency will be the difference between the frequencies of the two circuits and the amplitude will be additive and greater than either circuit alone. The range of the beat frequency is generated to be between a range of more than 250 Hz to about 15,000 Hz. Multiple levels of stimulation can be treated depending upon the electrode placement, pairing and modulation pattern selected. The range of output would be from about 0 volts to about 11 volts per circuit depending on the patient's needs and the pulse width is commonly set at 210 microseconds but it could range from about 10-600 microseconds. The amplitude can be modulated in the respective circuits to increase the area of targeted stimulation. This type of current (interferential) provides improved directional control, decreased accommodation or habituation and increased depth of penetration in comparison to other standard implantable stimulation systems and their accompanying surgical leads. The amplitudes of the outputs in the respective circuits may be modulated to increase the area of targeted stimulation. Interferential current allows improved directional control and depth of penetration in comparison to other stimulation techniques. Thus, by generating the beat frequency signal, the resultant additive signal is directionally controlled to avoid cerebrospinal fluid proximate to the subject's spinal cord.

Within examples, to target specific areas of the spinal cord using modulation of the circuit outputs and the resultant beat frequency signal would be directionally controlled and/or depths of penetration are controlled.

Within examples, using an electrical stimulator that includes electrodes implanted upon the dura mater with interferential currents produces a beat frequency signal that has deeper penetration than that possible using traditional SCS stimulation, and a majority of the beat frequency signal can be more precisely controlled in terms of direction and depth of tissue penetration proximate to the subject's spinal cord. Thus, interferential current may recruit larger numbers of dorsal column fibers and potentially provide greater levels of pain relief and benefit to intractable pain patients. Further, providing an interferential component to the electrode array of the SCS allows the crossing of the two signals such that the resultant additive effect of the beat frequency produces deeper penetration of the signal and a higher resultant amplitude at the stimulation site because only sub-threshold signals, of minimal biological consequence, remain in or shunt through the CSF. Because most of the current in conventional SCS remains in the CSF, it does not project deeply into the dorsal column. In contrast, providing an interferential component allows deeper penetration of the signal. Thus, the signal does not remain in the CSF.

Briefly described, in architecture, an example apparatus may include digital signal processors (DSPs) for improving the accuracy and reliability of digital signals. Digital signal processing works by standardizing or clarifying the output of a digital signal. In this embodiment, the digital signal processor is used to shape multiple pulsatile waveforms to approximate the output of a sine-wave generator. In other examples, the digital signal processor can be replaced with a field programmable gate array (FPGA). An FPGA is an integrated circuit that can be programmed in the field after it is manufactured and therefore allows users to adjust the circuit output as the needs change. Both the DSP and the FPGA process a digital signal into a pseudo-sine-wave current waveform from the digital pulses generated by a pulse generator. The pseudo-sine-wave current waveform can be transmitted through implantable quadripolar leads with eight electrodes at a targeted area creating a pair of interferential currents.

FIG. 1 shows a stimulator 100 for the electrical stimulation of the spinal cord utilizing an interferential current 110 that has a base medium frequency alternating current within the range of about 500 Hz-20 KHz.

By the term "about" and/or the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

The interferential current 110 is set up between two circuits 118, 120 that are arranged in a cross-pattern. A first pair of implantable electrodes 108a-b are positioned on a subject's spinal column 112, preferably the dorsal column, at one set of diagonal corners of a targeted area. A second pair of implantable electrodes 108c-d is then positioned at the other set of diagonal corners of the targeted area. The electrodes 108 are attached to the dura matter in the epidural space at predetermined locations proximate to the spinal cord. A digital signal processor 102 is connected to the first and second pairs of surface electrodes 108a-b and 108c-d. When a signal generating source 104 is connected to the digital signal processor 102, a sine-wave-like waveform signal output 106 is created. The digital signal processor 102 improves the accuracy and reliability of digital signals. The digital signal processor 102 processes multiple pulses 116 from the signal generating source 104 to approximate a sine-wave (pseudo-sine-wave or sine-wave-like). Thus, that type of current recruits larger numbers of dorsal column fibers and provides greater levels of pain relief. In some examples, as a result of recruiting larger numbers of dorsal column fibers by using interferential current and by generating a beat frequency signal, the patients could potentially experience greater levels of pain relief.

The digital signal processor 102 generates individual pulses 106 of differing widths and resultant amplitudes. In some examples, the pulse width is set at 210 microseconds, but can range from 50-600 microseconds. When those differing pulses 106 are driven into a transformer (not shown), the pseudo-sine-wave is produced. A pulse generator 104 is connected to the digital signal processor 102 and supplies the pulsed digital signal output 116 to the digital signal processor 102. The digital signal 106 processed by the digital signal processor 102 creates the first circuit 118 and the second circuit 120 at the first and second pairs of surface electrodes 108a-b and 108c-d, respectively. Within examples, a range of output of the electrical circuits 118, 120 is about 0-11 volts per circuit, depending on the patient's needs for pain treatment. Where the first and second circuits 118, 120 superimpose (cross), the resultant beat frequency (which may be between 1 and 250 beats/second) will be the difference between the frequencies of the two circuits, and the amplitude will be additive and greater than either circuit alone. Within other examples, the resultant beat frequency signal may have a frequency within a range of more than 250 Hz to about 15,000 Hz.

The signal generating source 104 may be an interferential current generator that generates an interferential output including first and second signals having different first and second frequencies. First ends of the implantable electrodes 108a and 108d are connected to the interferential current generator 104 and second ends 108b and 108c are configured to be implanted to a dura matter in an epidural space at predetermined locations proximate to a subject's spinal cord. The two pairs of implantable electrodes 108a-b and 108c-d carry one of the first and second signals such that the first and second frequencies interfere with each other to produce at least one beat signal proximate to the subject's spinal cord.

A field-programmable gate array (not shown) can also be used to shape multiple pulsatile waveforms to approximate the output of a sine-wave generator instead of or in addition to the digital signal processor 102 described above. The FPGA is an integrated circuit that can be programmed in the field after it is manufactured and allows its user to adjust the circuit output as desired. Thus, in an alternative embodiment, the digital signal processor may be replaced with the FPGA. Whereas DSP processors typically have eight dedicated multipliers at their disposal, an FPGA device can offer 224 dedicated multipliers plus additional logic element-based multipliers as needed. That allows for complex digital signal processing applications such as finite impulse response filters, forward error correction, modulation-demodulation, encryption and applications.

Figure 2:
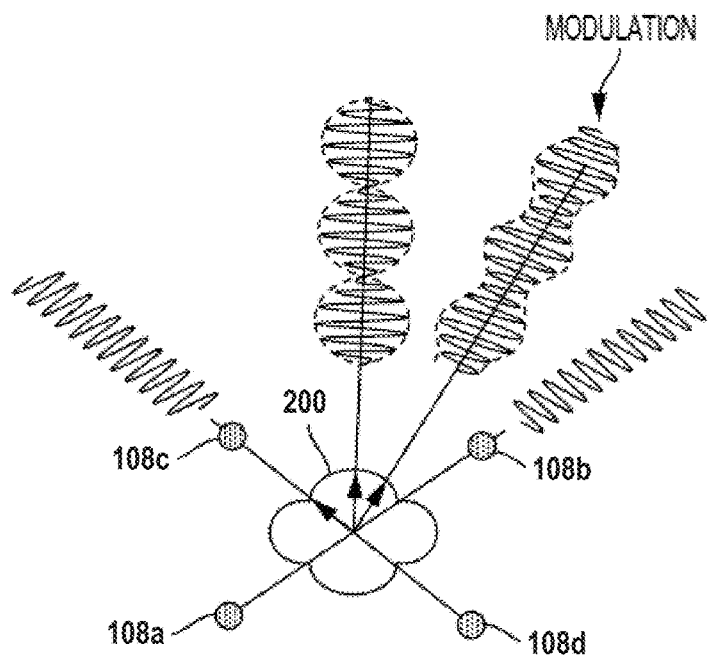
FIG. 2 is a perspective view of an interferential current pattern indicating the current intensity level and area of beat frequency formation, according to an example embodiment.

FIG. 2 illustrates an example perspective view of an interferential current pattern indicating the current intensity level and area of beat frequency formation, according to an example embodiment. The first pair of implantable electrodes 108a-b are shown positioned on the subject's spinal column at one set of diagonal corners of a targeted area 200, and the second pair of implantable electrodes 108c-d are then positioned at the other set of diagonal corners of the targeted area 200. Where the first and second circuits superimpose (cross), the resultant beat frequency will be the difference between the frequencies of the two circuits, and the amplitude will be additive and greater than either circuit alone in the target area 200.

As shown in FIG. 2, the first pair of implantable electrodes 108a-b and the second pair of implantable electrodes 108c-d are positioned in a crossing configuration such that a first circuit created between the first pair of implantable electrodes crosses a second circuit created between the second pair of implantable electrodes.

Within examples, altering the targeted area 200 of the subject's spinal cord can be performed by modulating amplitudes of the signals, as shown in FIG. 2. Thus, multiple target areas of the spinal cord can be treated depending upon the quantity and placement of the first and second pairs of electrodes, and by modulating the amplitudes of the outputs of the first and second circuits.

Figure 3:
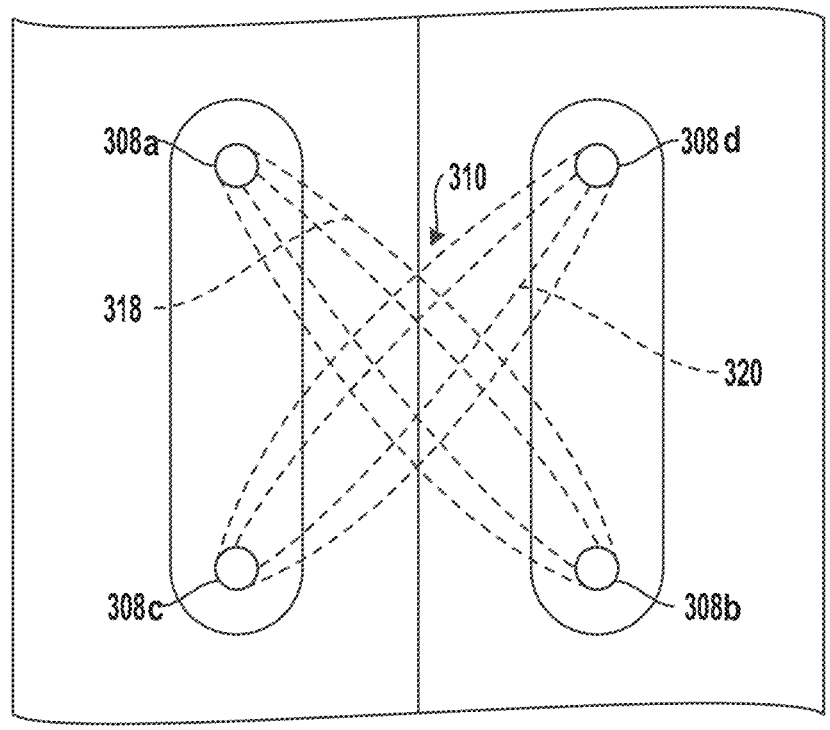
FIG. 3 is a perspective view illustrating the effective area of stimulation resulting from the crossing of separate circuits, according to an example embodiment.

FIG. 3 is a perspective view illustrating the effective area of stimulation resulting from the crossing of separate circuits, according to an example embodiment. Electrode pairs 308a-b and 308c-d are shown in a crossing pattern creating first and second circuits 318 and 320. Modulating outputs of the first and second circuits 318 and 320 increases the area of the targeted stimulation. The depth of modulation can vary from 0 to 100% and depends on the direction of the currents established by the first and second circuits 318 and 320. It has been shown that when the first and second circuits 318 and 320 intersect at 90°, the maximum resultant amplitude and the deepest level of modulation is half-way between the two circuits (450 diagonally) as shown at the intersection 310. Hence, the target area of stimulation can be augmented by modulation of the amplitudes of the outputs of the two circuits.

Figure 4:
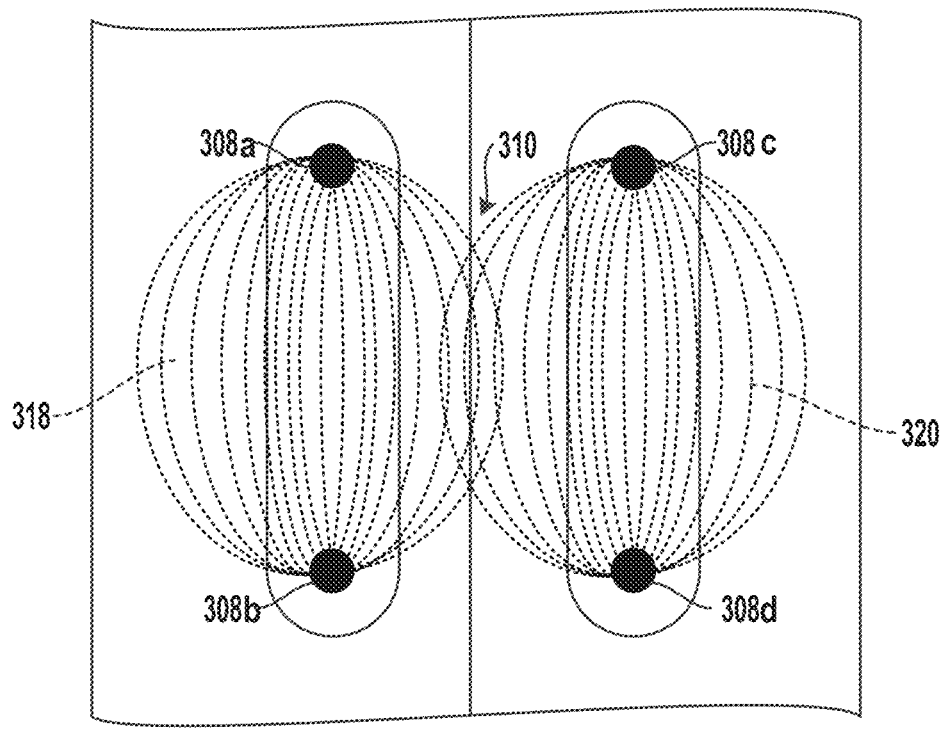
FIG. 4 is a perspective view illustrating an effective area of stimulation resulting from a parallel configuration of the separate circuits, according to an example embodiment.

FIG. 4 is a perspective view illustrating another example configuration of the implantable electrodes. In this example, the first pair of implantable electrodes 308a-b and the second pair of implantable electrodes 308c-d are positioned in a parallel configuration such that a first circuit 318 created between the first pair of implantable electrodes 308a-b is parallel to a second circuit 320 created between the second pair of implantable electrodes 308c-d.

Beat frequency signals can be generated when the circuits are in a parallel configuration as shown in FIG. 4, and there is an alignment of the generated fields. In a band 310 where both fields align, there is a more focusable beat field that produces a controllable peak of amplitude within the modulation envelope. The area of overlap and concentration in the parallel electrode configuration can be maximized by biasing the electrodes so as to achieve aligned fields in the region of concentration (target). Biasing may be performed such that an anode and cathode of one pair of implantable electrodes are aligned vertically (longitudinal) and an anode and cathode of the other pair of implantable electrodes are aligned vertically (longitudinal) proximal to each other to form an area of overlap, and agreement with the beat frequency in between the two channels (circuits), as shown in FIG. 4.

In addition, biasing the first pair of implantable electrodes 308a-b and the second pair of implantable electrodes 308c-d may be performed to cause the first field and the second field 318 and 320 to be unaligned for an untargeted region of concentration. Thus, in areas other than proximal to the target region, the beat frequency signal will be minimal and ineffective.

A horizontal distance between the two channels may be about between 1 mm and 5 mm, for example. Additionally, the first pair of implantable electrodes 308a-b may be positioned at a longitudinal (edge to edge) separation distance of about 2 mm to 10 mm, and the second pair of implantable electrodes 308c-d may be positioned at a longitudinal (edge to edge) separation distance of about 2 mm to 10 mm, for example.

Figure 5:
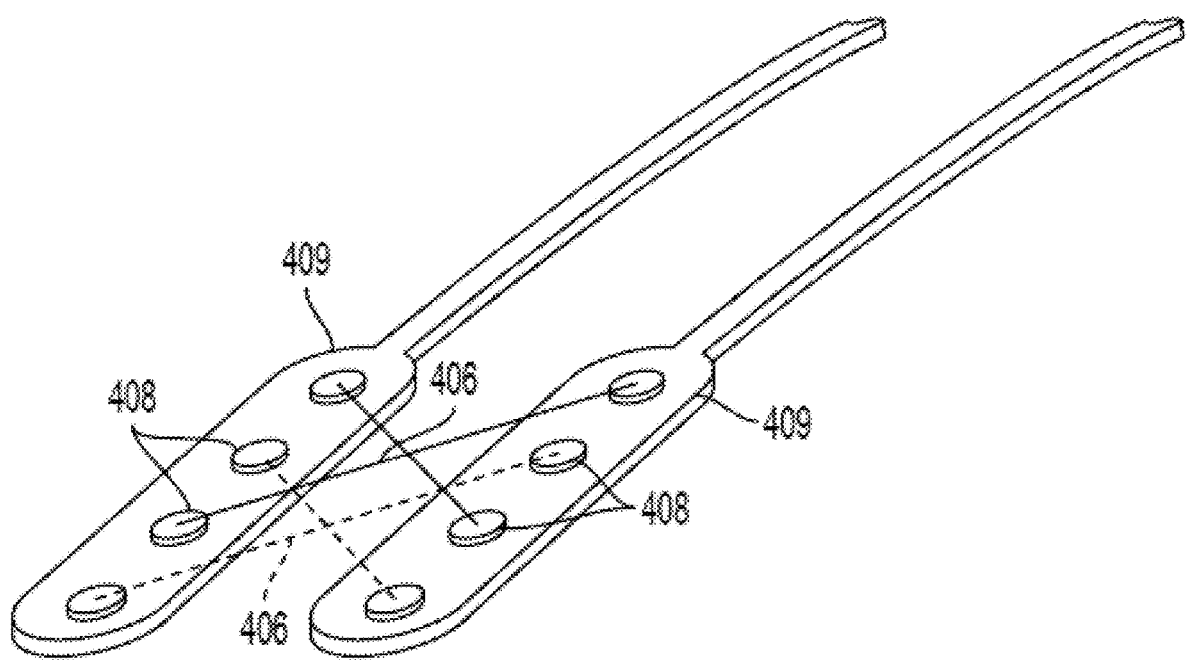
FIG. 5 illustrates an example implantable electrode arrangement, according to an example embodiment.

FIG. 5 illustrates an example implantable electrode arrangement. FIG. 5 illustrates two interferential currents 406 with sine-wave-like waveforms that are produced by two implantable quadripolar leads 409. Each quadripolar lead 409 includes four electrodes 408 for a total of eight. The two quadripolar leads 409 allow a greater target treatment stimulation area of the spinal cord. However, electrical stimulators of the present disclosure may also apply to the use of two bipolar or octapolar lead systems, and other suitable devices. The electrodes could be activated in various combinations and patterns, and not just as shown in the drawings.

Thus, in FIG. 5, leads 409 are shown to include four electrodes each, although any number of electrodes may be included such as six, eight, ten, . . . , or up to thirty or thirty-two, for example. Pairs of implantable electrodes are created between the electrodes on the leads 409. Pairs may be created between electrodes on the same lead (so as to create a parallel configuration), or between electrodes on different leads, as shown in FIG. 5 to create a crossing configuration.

Figure 6:
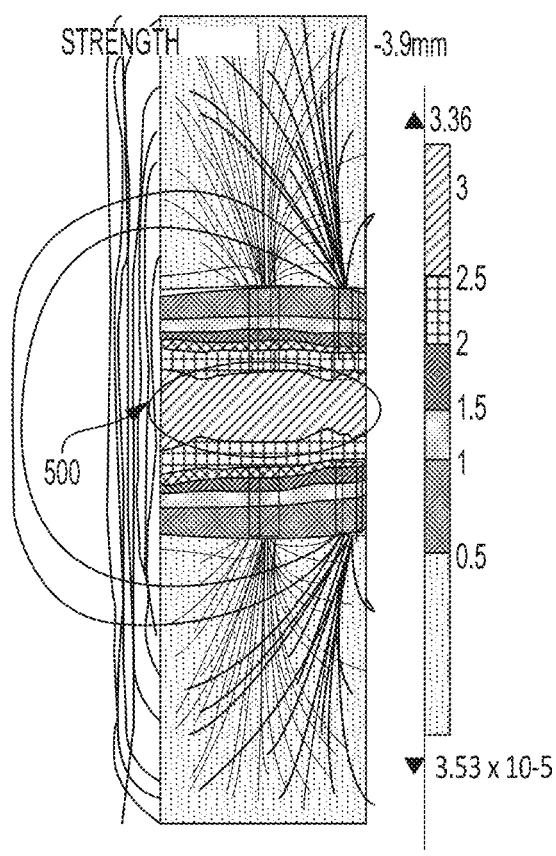
FIG. 6 illustrates a field strength view of a simulation of a 3D model of the electrical stimulator in a parallel configuration, according to an example embodiment.

Separating the electrode pairs may cause a difference in their field strength toward the lateral extremes. FIG. 6 illustrates a field strength view of a simulation of a 3D model of the electrical stimulator in a parallel configuration. FIG. 6 shows strength of a total field as though the electrodes/circuits had the same frequency, and so no interferential field is generated. As seen, strength of the field is maximum in a center area 500, however, the field spreads laterally along a target area and is not well confined.

Figure 7:
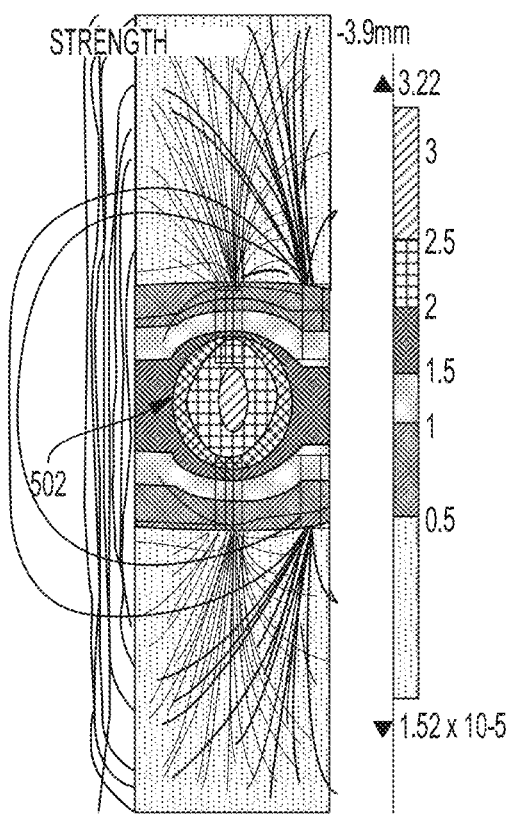
FIG. 7 illustrates another field strength view of a simulation of a 3D model of the electrical stimulator in a parallel configuration, according to an example embodiment.

FIG. 7 illustrates another field strength view of a simulation of a 3D model of the electrical stimulator in a parallel configuration. In FIG. 7, the simulation is performed with different frequencies provided to the electrodes/circuits to generate an interferential current. Thus, in FIG. 7, strength of the interferential field is shown in a center area 502. The parallel bias produces a central region where the two fields are equal and aligned to form a focused modulation beat frequency envelope on a target area.

Figure 8:
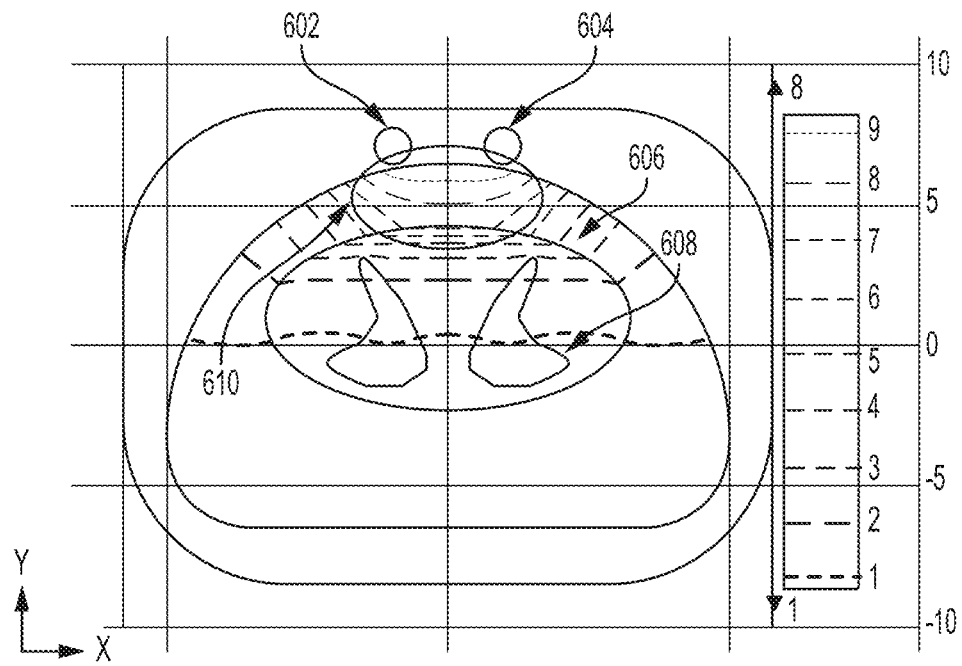
FIG. 8 illustrates an example field strength view across the spinal column as though the electrodes were biased with a single frequency, according to an example embodiment.

FIG. 8 illustrates an example field strength view across the spinal column as though the electrodes were biased with a single frequency. In FIG. 8, electrodes 602 and 608 are implanted to a dura matter 606, and provide penetration to a pyramid tract 608 of the spinal column. Similar to the simulation shown in FIG. 6, a field provided by the electrodes 602 and 604 in FIG. 8 is not well directed and a maximum strength of the field is not well confined to a target area 610. In FIGS. 6 and 8, darker field lines indicate a stronger field.

Figure 9:
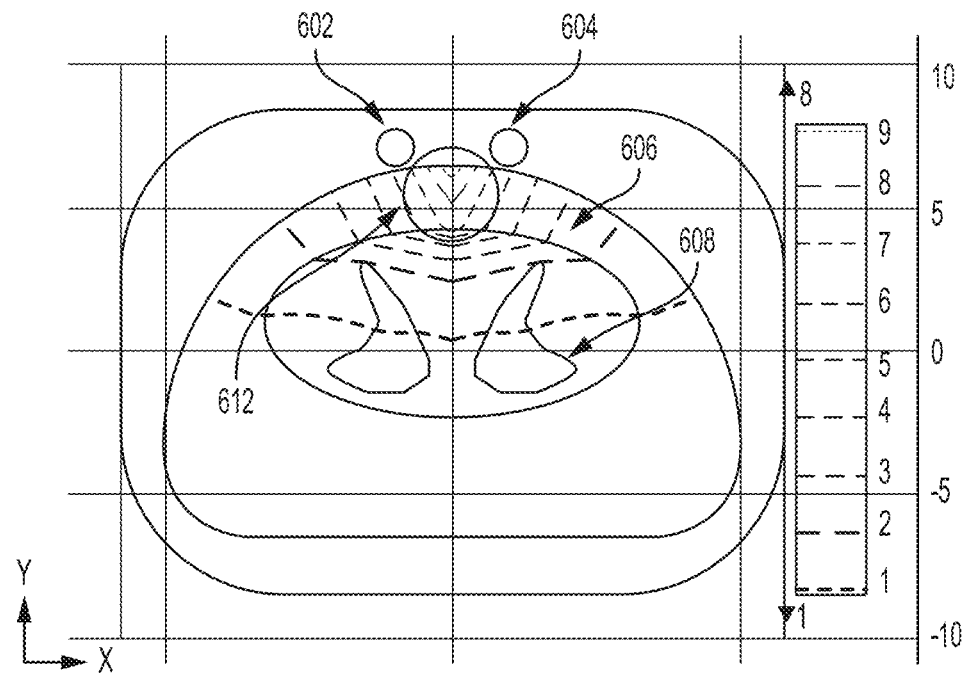
FIG. 9 illustrates another example field strength view across the spinal column as though the electrodes were biased with multiple frequencies, according to an example embodiment.

FIG. 9 illustrates another example field strength view across the spinal column as though the electrodes were biased with multiple frequencies. Similar to the simulation shown in FIG. 7, a field provided by the electrodes 602 and 604 in FIG. 9 includes an interferential field. A parallel bias produces a central region 612 where the two fields are about equal and aligned to provide a concentrated field at the target area.

A rostrocaudal field component in the models shown in FIGS. 8-9 is the z-component, Ez. A total field for non-interferential bias (e.g., FIG. 8) is given by a vector sum of the carrier fields. In a static solution, and maintaining phase between the two fields, Ez is a magnitude |E1z+E2z|. In FIG. 9, the interferential field is strongest where the two carrier fields are aligned, and if the two components are equal, the modulation envelope is 100%. If the two components are unequal, the modulation envelope is given by twice the magnitude of the lesser component. Thus, Ez is (2×min (|E1z|, |E2z|)), taking the magnitude individually because the phase relation changes over time.

Electrodes are placed and biased so as to produce alignment and equal strength for the component fields at a target area of a desired strong interferential signal. In addition, electrodes are placed such that either the fields are unaligned (e.g., perpendicular), or one of the components is weak at other areas for undesired interferential fields (e.g., untargeted areas). Either condition of unalignment or a weak component produces a weak interferential field.

Figure 10:
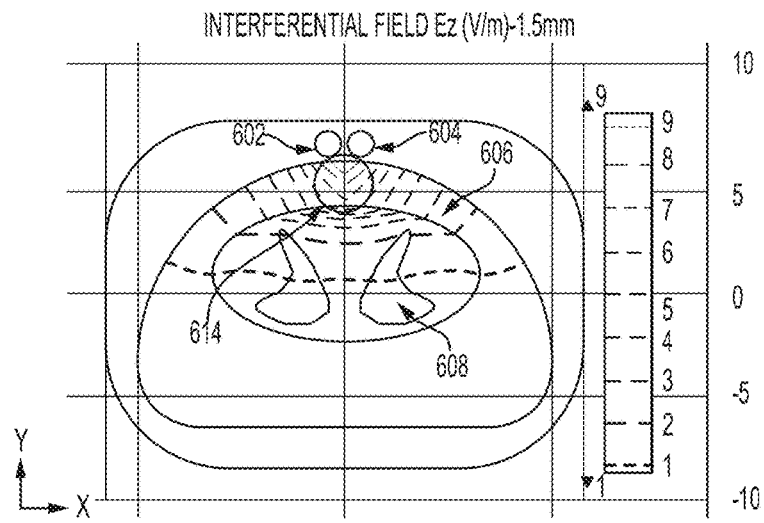
FIG. 10 illustrates further example field strength views across the spinal column as though the electrodes were biased with multiple frequencies and with variations in the electrode spacing, according to an example embodiment.
Figure 11:
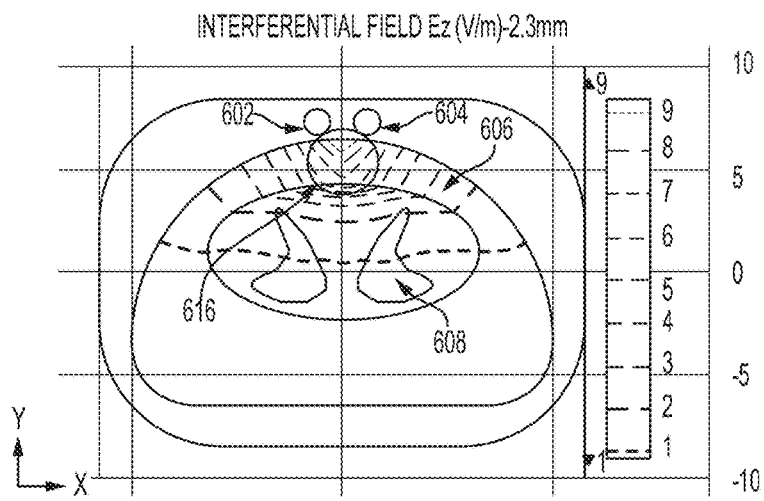
FIG. 11 illustrates further example field strength views across the spinal column as though the electrodes were biased with multiple frequencies and with variations in the electrode spacing, according to an example embodiment.
Figure 12:
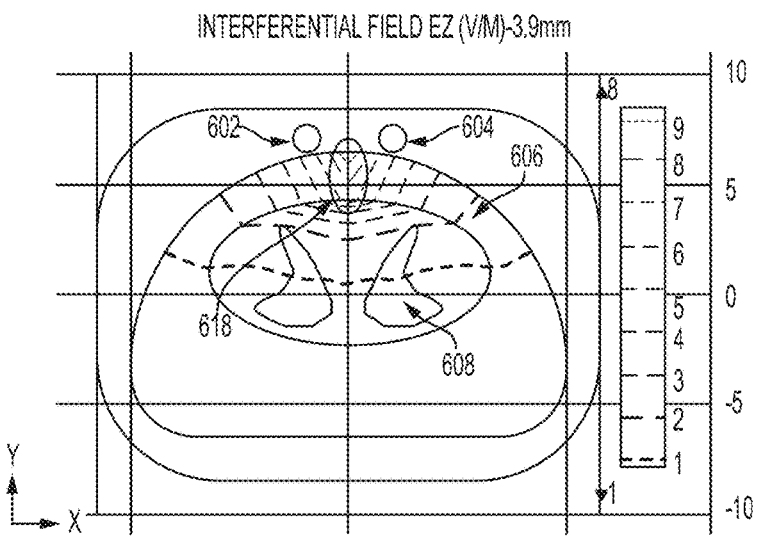
FIG. 12 illustrates further example field strength views across the spinal column as though the electrodes were biased with multiple frequencies and with variations in the electrode spacing, according to an example embodiment.

FIGS. 10-12 illustrate further example field strength views across the spinal column as though the electrodes were biased with multiple frequencies and with variations in the electrode spacing. In FIGS. 10-12, an interferential field is generated and directed to target areas 614, 616, and 618. Horizontal separation of the electrodes 602 and 604 can affect a depth and spreading of penetration. For example, FIG. 10 illustrates the electrodes at about 1.5 mm separation, FIG. 11 illustrates the electrodes 602 and 604 at about 2.3 mm separation and FIG. 12 illustrates the electrodes 602 and 604 at about 3.9 mm separation. The variance of the shape of the field appears optimized at a spacing of about 2.3 mm, however, selective depth of penetration can be achieved using spacing from about 1 mm to about 5 mm, for example.

Figure 13:
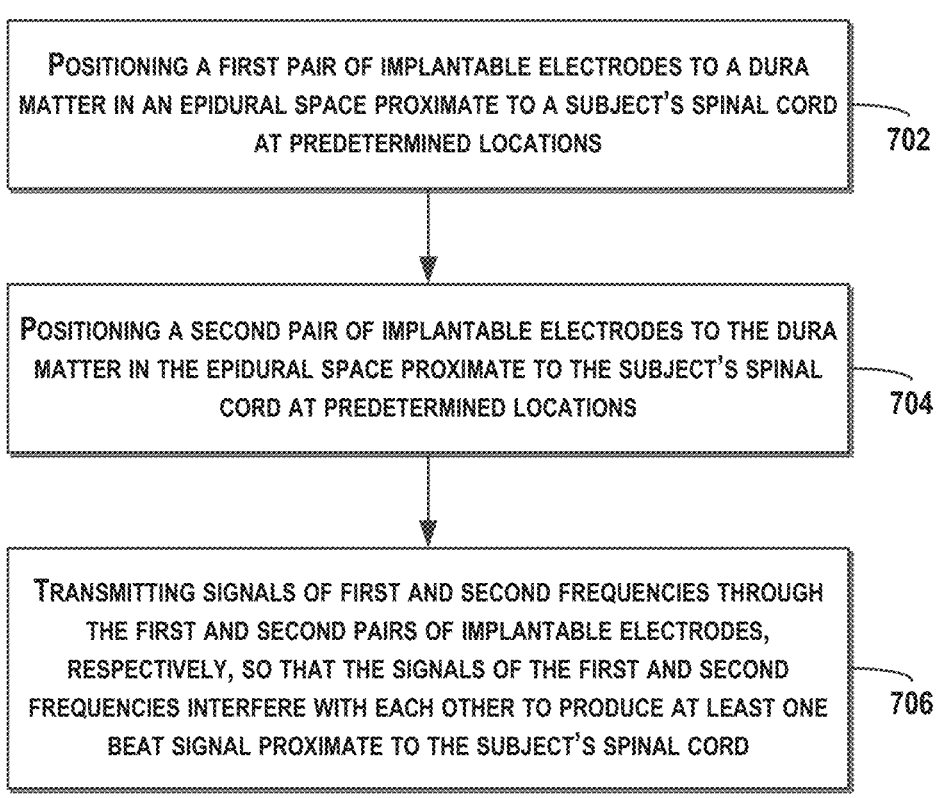
FIG. 13 shows a flowchart of an example method for spinal cord stimulation treatment using electrical stimulation of a spinal cord, according to an example embodiment.

FIG. 13 shows a flowchart of an example method for spinal cord stimulation treatment using electrical stimulation of a spinal cord, according to an example embodiment. The method shown in FIG. 13 presents an embodiment of a method that, for example, could be used by the stimulator shown in FIG. 1, for example, and may be performed by components of the stimulator in FIG. 1. In some instances, components of the stimulator may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. The method may include one or more operations, functions, or actions as illustrated by one or more of blocks 702-706. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 702, the method includes positioning a first pair of implantable electrodes to a dura matter in an epidural space proximate to a subject's spinal cord at predetermined locations. At block 704, the method includes positioning a second pair of implantable electrodes to the dura matter in the epidural space proximate to the subject's spinal cord at predetermined locations.

As described, the first pair of implantable electrodes and the second pair of implantable electrodes may be positioned in a crossing configuration such that a first circuit created between the first pair of implantable electrodes crosses a second circuit created between the second pair of implantable electrodes. In another example, the first pair of implantable electrodes and the second pair of implantable electrodes may be positioned in a parallel configuration such that a first circuit created between the first pair of implantable electrodes is parallel to a second circuit created between the second pair of implantable electrodes. In these examples, the first circuit and the second circuit generate a first field and a second field, and the first pair of implantable electrodes and the second pair of implantable electrodes are positioned such that the first field and the second field overlap to produce the at least one beat signal.

At block 706, the method includes transmitting signals of first and second frequencies through the first and second pairs of implantable electrodes respectively, so that the signals of the first and second frequencies interfere with each other to produce at least one beat signal proximate to the subject's spinal cord. The at least one beat signal has a frequency within a range of more than 250 Hz to about 15,000 Hz.

Within examples, the method includes transmitting signals of first frequencies of about 20,000 Hz through the first pair of implantable electrodes, transmitting signals of second frequencies of about 10,000 Hz through the second pair of implantable electrodes, and the signals of the first and second frequencies interfere with each other to produce the at least one beat signal proximate to the subject's spinal cord of about 10,000 Hz.

In other examples, the method includes transmitting signals of first frequencies of about 20,000 Hz through the first pair of implantable electrodes, transmitting signals of second frequencies of about 5,000 Hz through the second pair of implantable electrodes, and the signals of the first and second frequencies interfere with each other to produce the at least one beat signal proximate to the subject's spinal cord of about 15,000 Hz.

Frequencies of signals may be transmitted through the first and second pair of implantable electrodes within ranges of about 0 to about 20,000 Hz, or any ranges than can result in a beat signal having a frequency in a range of more than 250 Hz to about 15,000 Hz. The beat signal frequency results from interference of the two signals from the first and second pair of implantable electrodes (e.g., for a frequency of 2,000 Hz at the first pair of implantable electrodes creating a first field interfering with a second field generated by the second pair of implantable electrodes due to a frequency of 12,000 Hz results in a beat signal frequency of about 10 k Hz).

Based on combinations of the first and second frequencies, the beat signal may be in a range of more than 250 Hz to about 15,000 Hz. Other examples of the beat signal include a signal in a range of frequency between about 3,000 Hz to about 15,000 Hz, a range of frequency between about 5,000 Hz to about 15,000 Hz, a range of frequency between about 10,000 Hz to about 15,000 Hz, a range of frequency between about 12,000 Hz to about 15,000 Hz, a range of frequency of more than 250 Hz to about 10,000 Hz, a range of frequency between about 3,000 Hz to about 5,000 Hz, a range of frequency between about 3,000 Hz to about 10,000 Hz, a range of frequency between about 3,000 Hz to about 12,000 Hz, a range of frequency between about 5,000 Hz to about 10,000 Hz, a range of frequency between about 7,000 Hz to about 10,000 Hz, a range of frequency between about 7,000 Hz to about 12,000 Hz, a range of frequency between about 12,000 Hz to about 15,000 Hz, or any other ranges between 250 Hz to about 20,000 Hz.

Example ranges of frequencies for the beat signal frequency may span a few hundred Hz, a few thousand Hz, or a few tens of thousands of Hz.

A range of the beat signal frequency may be in a lower range, such as more than 250 Hz to about 3,000 Hz, or within a middle range such as between about 3,000 Hz to about 7,000 Hz, or a high range such as between about 7,000 Hz to about 15,000 Hz. Any range or overlapping ranges between more than 250 Hz to about 15,000 Hz may be generated for the beat signal frequency.

Figure 14A:
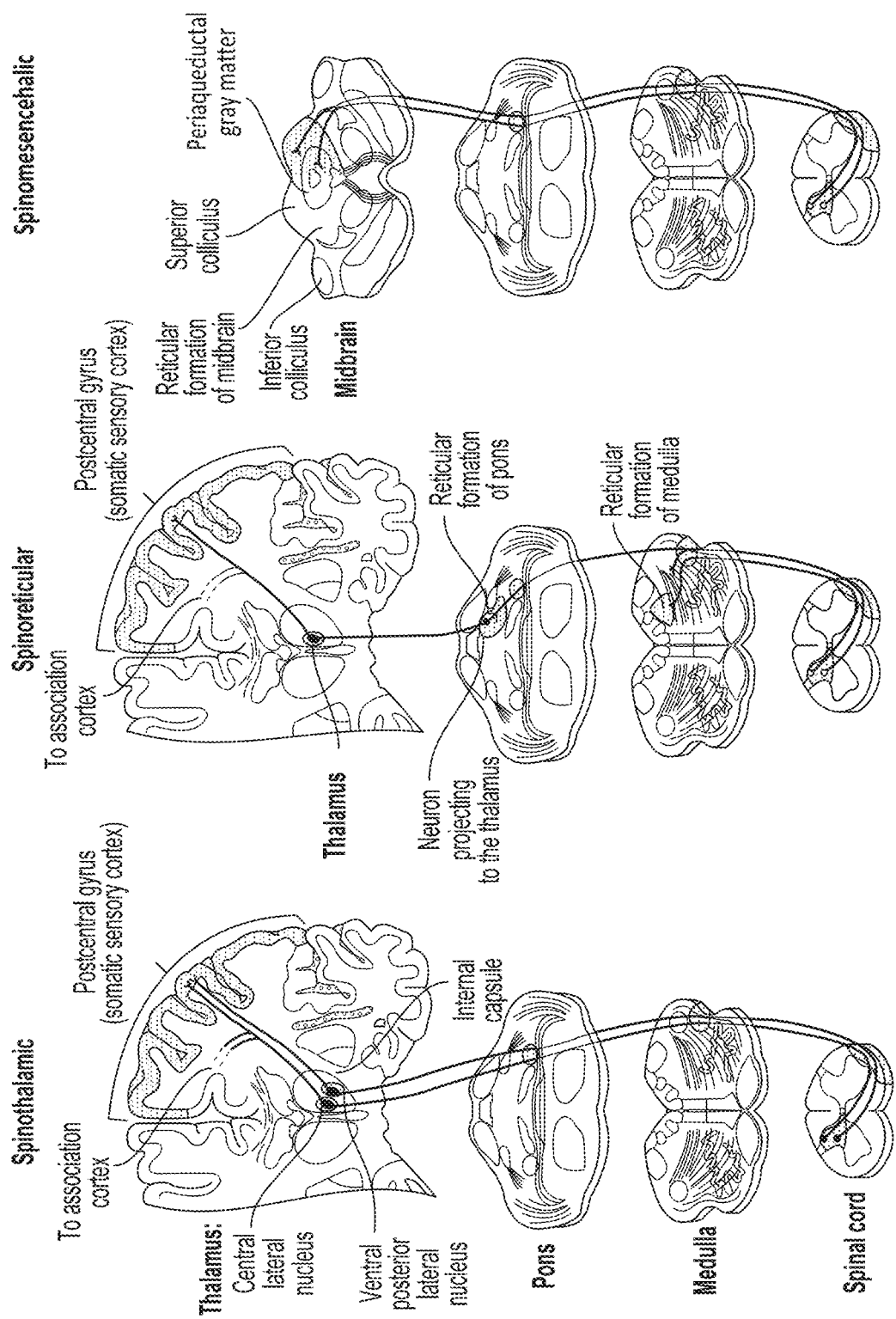
FIG. 14A illustrates an example of the spinothalamic, spinoreticular, spinomesencephalic tracts, according to an example embodiment.
Figure 14C:
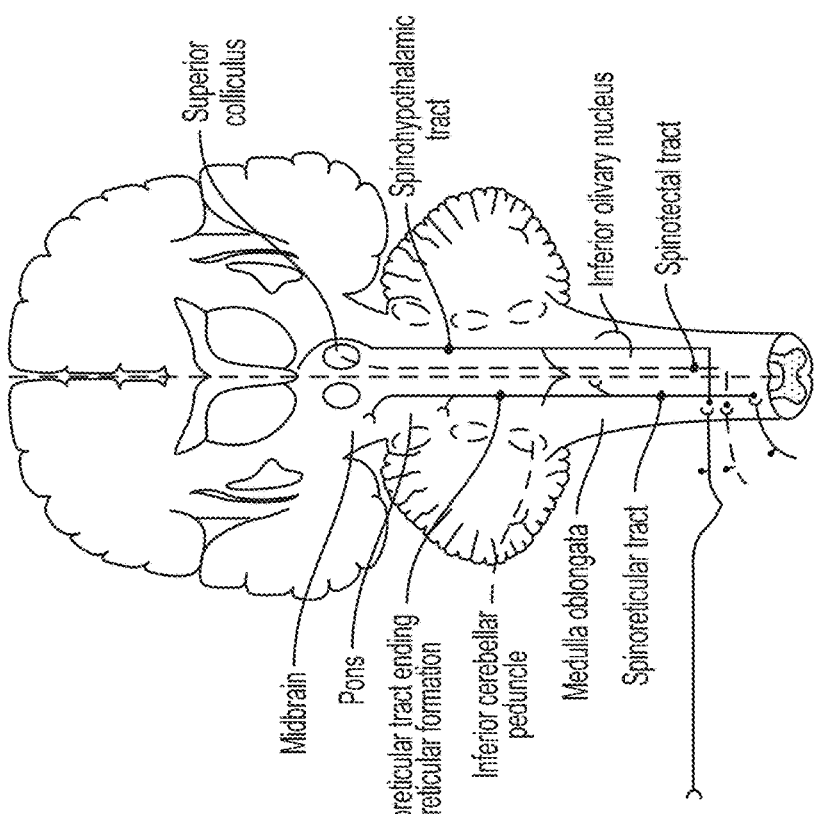
FIG. 14C illustrates an example of the spinohypothalamic tract, according to an example embodiment.
Figure 14B:
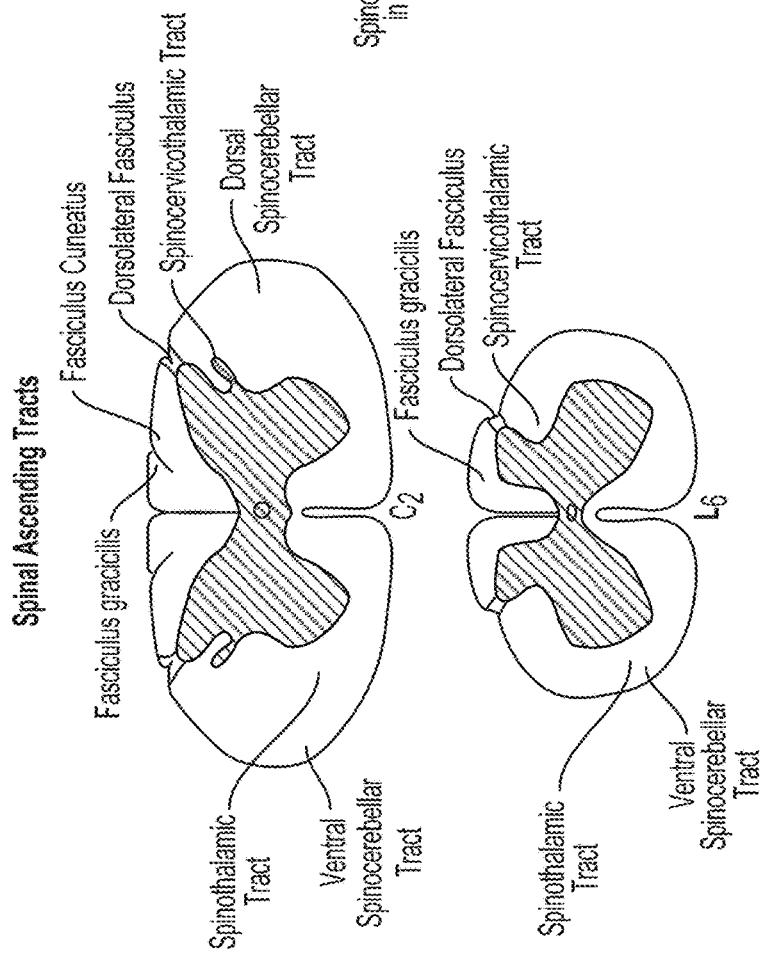
FIG. 14B illustrates an example of the cerviocothalamic tract, according to an example embodiment.

Within examples, forming a beat signal at a frequency at ranges described herein allows the signal to reach deeper into the dorsal column, and enables the signal to affect the membrane potential on other deeper structures of the spinal cord. Nociceptive information is transmitted from the spinal cord to the thalamus via five major ascending pathways including the spinothalamic, spinoreticular, spinomesencephalic, cerviocothalamic and spinohypothalamic tracts. FIG. 14A illustrates an example of the spinothalamic, spinoreticular, spinomesencephalic tracts, FIG. 14B illustrates an example of the cerviocothalamic tract, and FIG. 14C illustrates an example of the spinohypothalamic tract. Using examples herein, the beat signal may be directionally controlled deep into the subject's tissue proximate to one or more of these ascending pathways, and avoiding the at least one beat signal remaining in and shunting through cerebrospinal fluid proximate the subject's dorsal column.

Some standard spinal cord stimulation for pain uses low frequencies of 40 to 100 Hz for beat signals, and focuses on maximizing stimulation of the dorsal column. Other systems use medium frequency stimulation and do not generate action potentials, but rather produce "non-paresthesia" stimulation of the spinal cord. In other words, the patient does not feel any buzzing or stimulation in the areas of pain. The onset of action takes very long, and usually takes effect from 12 to 16 hours after is initiated. Because the patient does not feel the stimulation and action potentials are not being generated, the logical mechanism of action may be that this medium frequency output is affecting the membrane potential of the outer areas of the cord and potentially decreasing hyperactivity of the neurons which would be perceived as less pain.

Within examples herein, the signals of first and second frequencies may be transmitted through the first and second pairs of implantable electrodes respectively, so that the signals of the first and second frequencies interfere with each other to produce at least one beat signal proximate to the subject's spinal cord and produce a paresthesia-type beat signal, such that a subject may feel the signal. In this way, the subject can help with placement of the electrodes and stimulation of a target area is properly performed.

Additionally, as described above, electrodes can be placed to a dura matter in an epidural space proximate the subject's spinal cord to produce at least one beat signal proximate to the subject's spinal cord, and avoiding the at least one beat signal remaining in and shunting through cerebrospinal fluid proximate the subject's dorsal column through directional control. Spacing of the electrodes further enables directional control of the beat signal.

The five major ascending pathways including the spinothalamic, spinoreticular, spinomesencephalic, cerviocothalamic and spinohypothalamic tracts are not the main targets of older standard SCS because they cannot generate fields deep enough in the tissue without causing undesirable side effects and shunting of the stimulation.

Example interferential SCS stimulation described herein with a beat frequency of more than 250 Hz to about 15 k Hz (e.g., such as in the range of 10 kHz to 15 kHz) is able to generate higher amplitude envelopes of current that can be directed to other areas of the cord and have effects on the ascending tracts that may not be able to be accomplished with standard SCS stimulation because the standard SCS cannot generate such effective beat frequencies and direct the higher amplitude envelopes. The higher beat frequencies (250 Hz to 15 kHz) would have the added benefit of overcoming capacitive resistance of interfaces between different tissue types and tissue membranes and allow passage of sub-threshold and threshold current to deeper layers of the spinal cord.

Figure 15:
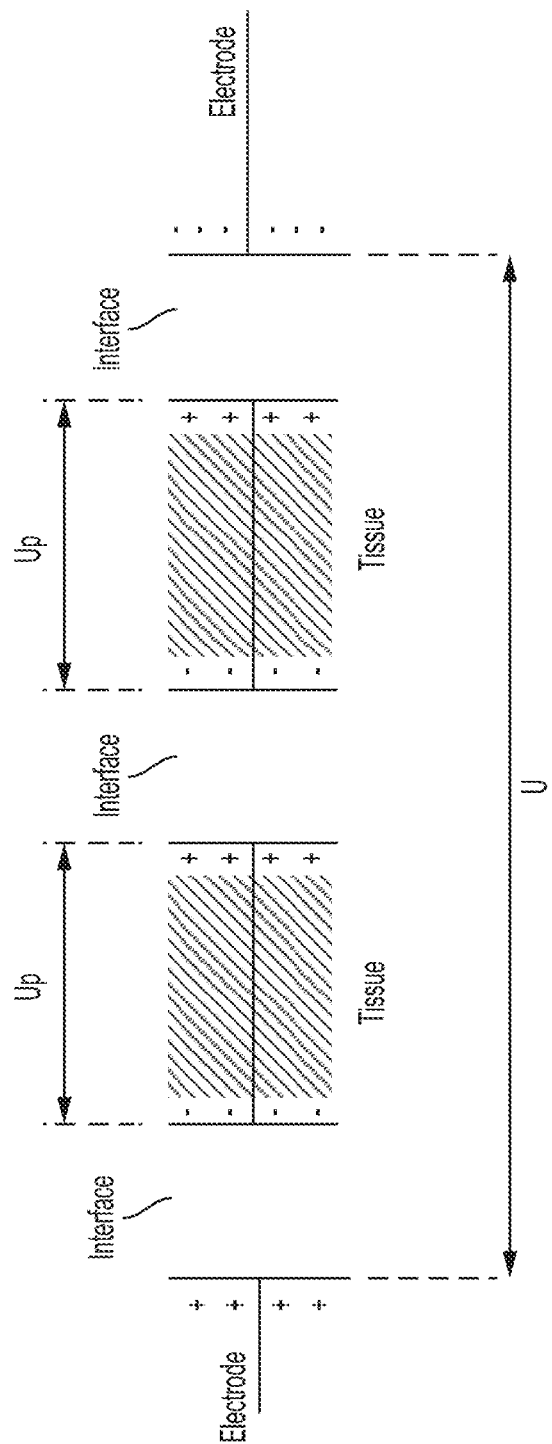
FIG. 15 illustrates an example diagram for capacitive resistance of tissue, according to an example embodiment.

FIG. 15 illustrates an example diagram for capacitive resistance of tissue. Separate tissue may be conceptually considered as having an interface between the tissue as shown. In FIG. 15, U is an applied voltage, and $U_p$ is a potential difference. The potential difference, $U_p$, is counter to the applied voltage, U, and develops a counter-voltage that is conceptually considered a reactance or capacitive resistance, X. A marked drop of the reactance of tissue interfaces at increased frequency is shown in the following formula:

$$X = \frac{1}{2\pi f C}$$

where X is capacitive resistance (reactance), f is frequency of the current, and C is polarization capacitance of the tissue.

For a 100 Hz alternating current, and C of $10^{-6}$, the reactance X is about 1600 ohms. For a 10 k Hz alternating current, the reactance X is about 16 ohms.

An interferential system of SCS that generates a higher beat frequency from 250 Hz to 15 kHz could penetrate deeper by generating a beat of 10 kHz to 15 kHz at a sub-threshold level for causing action potentials, and is sufficient to affect membrane potentials of other deeper structures of the cord including the five major ascending pathways directly rather than through dorsal column stimulation. Affecting these tracts and other deep structures of the cord can provide normalizing properties and potentially sooth hyperactivity in the tracts providing positive regulation of multiple symptoms other than pain such as cardiovascular, neuroendocrine, respiratory and emotional functions.

The electrical stimulator described herein may be fully implanted into a subject, or portions of the electrical stimulator may be implanted and portions remain exterior of the subject. As an example, the electrodes may be implantable, as described, and the interferential current generator and power source can be external and coupled to the implanted electrodes through wires. In other examples, coupling may occur through a wireless link (e.g., radio frequency (RF) link) from the current generator to the electrodes, such that the electrodes are implanted and the current generator is not implanted. The RF carrier frequency can be in the MHz, GHz or THz range and will induce a current in an implanted receiver that is linked or connected to the implantable electrodes. The RF carrier frequency can range from about 1 MHz through about 20 THz.

In still other examples, the interferential current generator is implantable in the subject (and a power source connected to the interferential current generator may be implanted as well), and the electrodes are further implanted. The interferential current generator may be implanted near or in the brachial plexus, or near or underneath the $12^{th}$ rib bone, for example.

Figure 16:
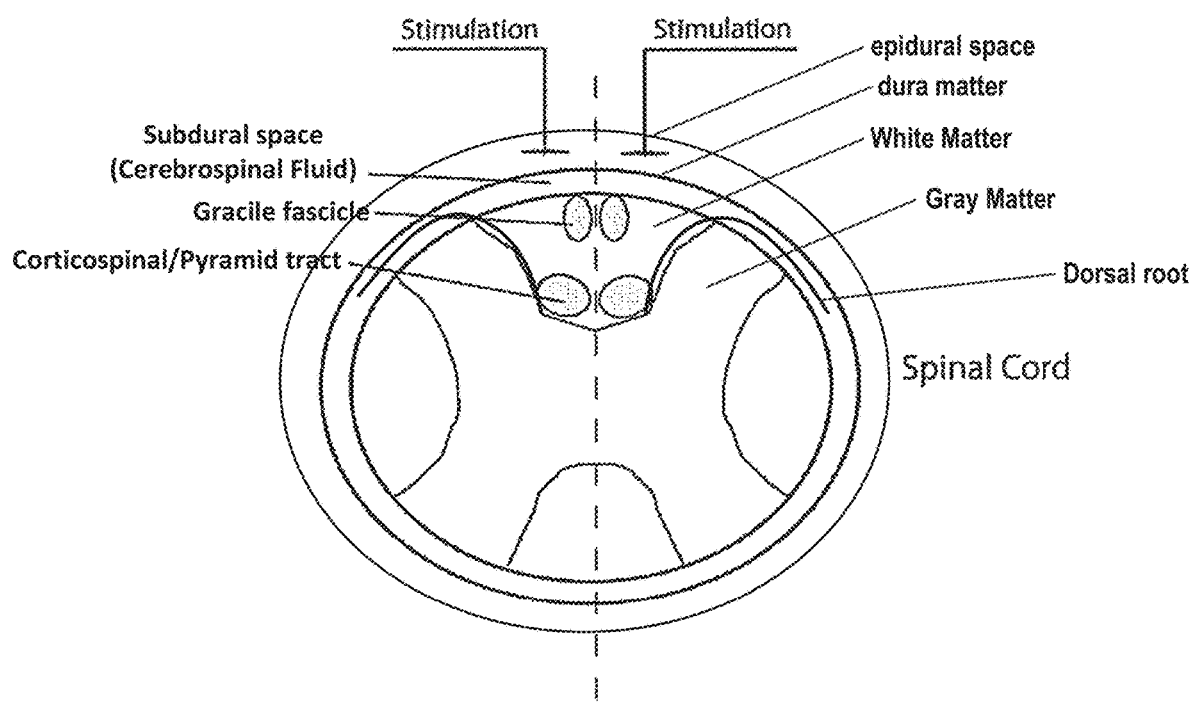
FIG. 16 illustrates the Gracile nucleus and Pyramid tract as ascending and descending tracts in the dorsal column of the spinal cord, according to an example embodiment.

Within examples, using the stimulator 100 in FIG. 1 for spinal cord stimulation (SCS) provides deep stimulation for effective pain relief. Effective pain relief can be achieved by activating one of the ascending pathways including the spinothalamic, spinoreticular, spinomesencephalic, cerviocothalamic and spinohypothalamic tracts, as described above. In addition, activation of the Gracile nucleus and Pyramid tract in the spinal cord may provide effective relief. FIG. 16 illustrates the Gracile nucleus and Pyramid tract as ascending and descending tracts in the dorsal column of the spinal cord, according to an example embodiment. The spinal cord is encased in a thick membrane called the dura mater, and inside a layer of the dura mater is cerebrospinal fluid, as shown in FIG. 16.

The cerebrospinal fluid is conductive, and stimulation that spreads through the fluid can cause pain if the current density becomes too high near the dorsal root ganglia that lie along a vertebral column by the spine. It is desired to provide deep stimulation through the dura mater of the spinal cord for activating the Gracile nucleus and Pyramid and other portions of the Dorsal Column using low levels of stimulation so as to avoid spreading of stimulation through the cerebrospinal fluid.

Using an interferential current SCS, stimulation may be provided deep through the dura mater with low current levels, thus lowering the threshold of activation of the Gracile nucleus and Pyramid. With spinal cord stimulation, if current is simply increased, the effect may be to spread stimulation through the cerebrospinal fluid, resulting in stimulation of the dorsal root ganglia, which causes chest and thoracic pain. Using an interferential current SCS method to directionally control stimulation, low levels of stimulation can be provided, and deep penetration through the dura mater can be achieved without spreading of the stimulation and resulting side effects.

Experiments using the interferential current SCS method were performed in the Neuronano Lund Research Center University in Sweden by Marcus Granmo and Jens Schouenborg. The results demonstrate that using the interferential electrical stimulator, a beat frequency is obtained that provides deep and localized stimulation.

The Experimental setup included adult rats (Sprague-Dawley, 200-230 grams) that were anesthetized with isoflurane gas (1.8% in a mixture of 60/40% $NO_2$ and oxygen), as described, for example, in Kalliomaki, J., Granmo, M., Schouenborg, J. Pain. 2003 Jul.; 104(1-2):195-200. FIGS. 3-4, described above, illustrate the setup of two pairs of stimulation electrodes (bipolar stimulation, 4 electrodes in total) that were placed epidurally (to a dura mater in an epidural space) on the spinal cord in two configurations: (i) a crossed configuration (FIG. 3) and (ii) a parallel configuration (FIG. 4). Recording microelectrodes were inserted in the Gracile nucleus and the Pyramid in the brainstem. The recording electrodes do not provide stimulation to the Gracile nucleus and the Pyramid tract. Simultaneous recordings from the Gacile nucleus and the Pyramid in the brainstem render comparison of the effect of stimulation. The Gracile nucleus receives ascending sensory information from dorsal column tracts that run relatively superficial in the dorsal part of the spinal cord. The pyramid, as part of the corticospinal tract, conveys descending motor commands from the brain to the spinal cord. In the rat spinal cord, the pyramidal tract is located deep in the dorsal column, i.e. deeper than the dorsal column of the spinal cord activating the Gracile nucleus. By spinal cord stimulation, activation of the pyramid tract fibers antidromically evoked volleys in this relatively deep tract that were recorded, thus giving information about depth of penetration of the stimulation. After each experiment, the animals were perfused with formalin and the caudal brain stem was sectioned to verify the electrode position in the brainstem.

Figure 17A:
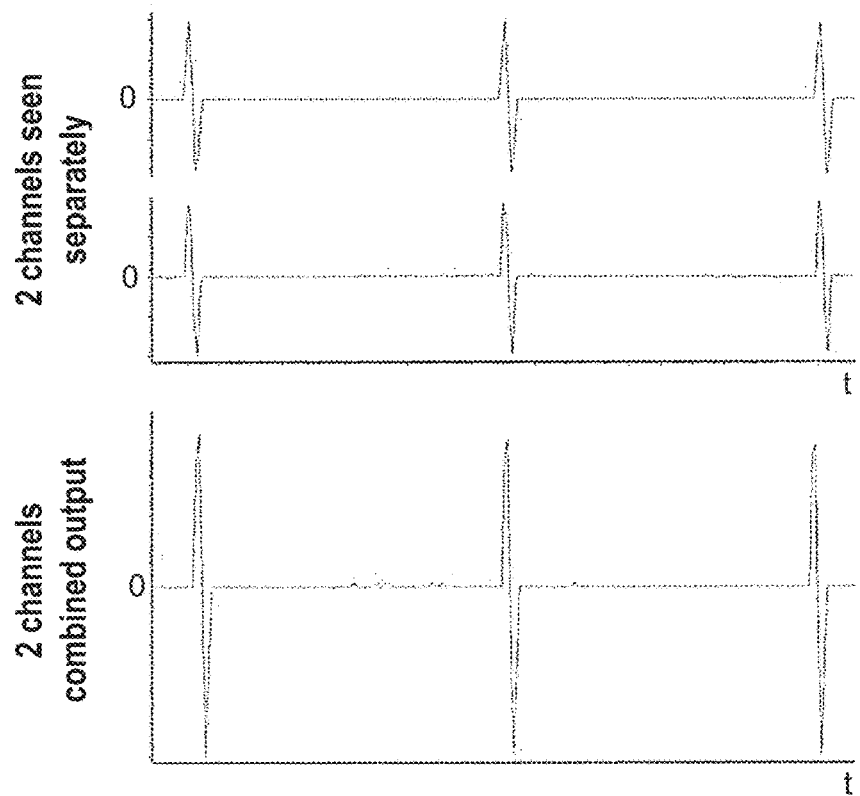
FIG. 17A illustrates a first stimulation using sinus waves of about 500 µs width (corresponding to 2000 Hz waves) applied at a frequency of about 100 Hz (e.g., pulsed sine waves of 500 µs width applied at a rate of 100 pulses per second corresponding to 2000 Hz waves) for a conventional stimulation, according to an example embodiment.

Experiments were performed using two types of stimulation paradigms, each of which was applied to both electrode pairs that were placed epidurally in the two configurations shown in FIGS. 3-4. FIG. 17A illustrates a first stimulation using sinus waves of about 500 μs width (corresponding to 2000 Hz waves) applied at a frequency of about 100 Hz (e.g., pulsed sine waves of 500 μs width applied at a rate of 100 pulses per second corresponding to 2000 Hz waves) for a conventional stimulation.

Figure 17B:
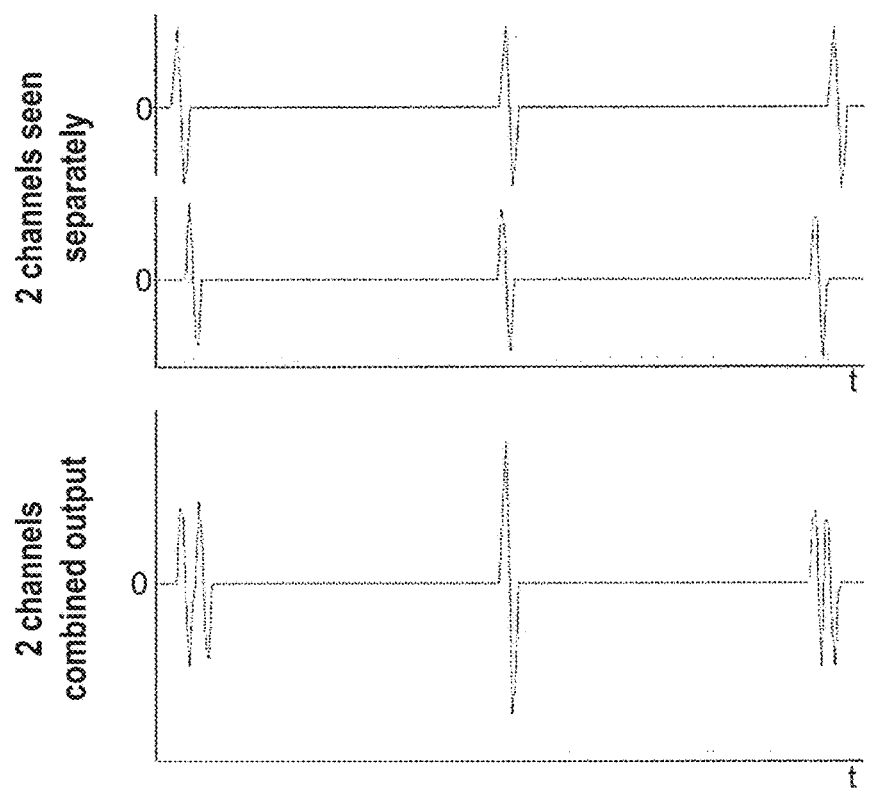
FIG. 17B illustrates a second stimulation using sinus waves of about 500 µs (corresponding to 2000 Hz) applied to one set of electrode pairs, and sinus waves of about 476 µs (corresponding to 2100 Hz) applied to the other set of electrode pairs to create an interference pattern, according to an example embodiment.

FIG. 17B illustrates a second stimulation using sinus waves of about 500 μs (corresponding to 2000 Hz) applied to one set of electrode pairs, and sinus waves of about 476 μs (corresponding to 2100 Hz) applied to the other set of electrode pairs to create an interference pattern. The sinus waves were applied at about 100 and about 105 Hz, respectively (e.g., pulsed sine waves of 500 μs width applied at a rate of 100 pulses per second corresponding to 2000 Hz waves, and pulsed sine waves of 476 μs width applied at a rate of 105 pulses per second corresponding to 2100 Hz waves). A resulting beat frequency signal of 100 Hz was produced proximate to the subject's spinal cord.

Figure 18:
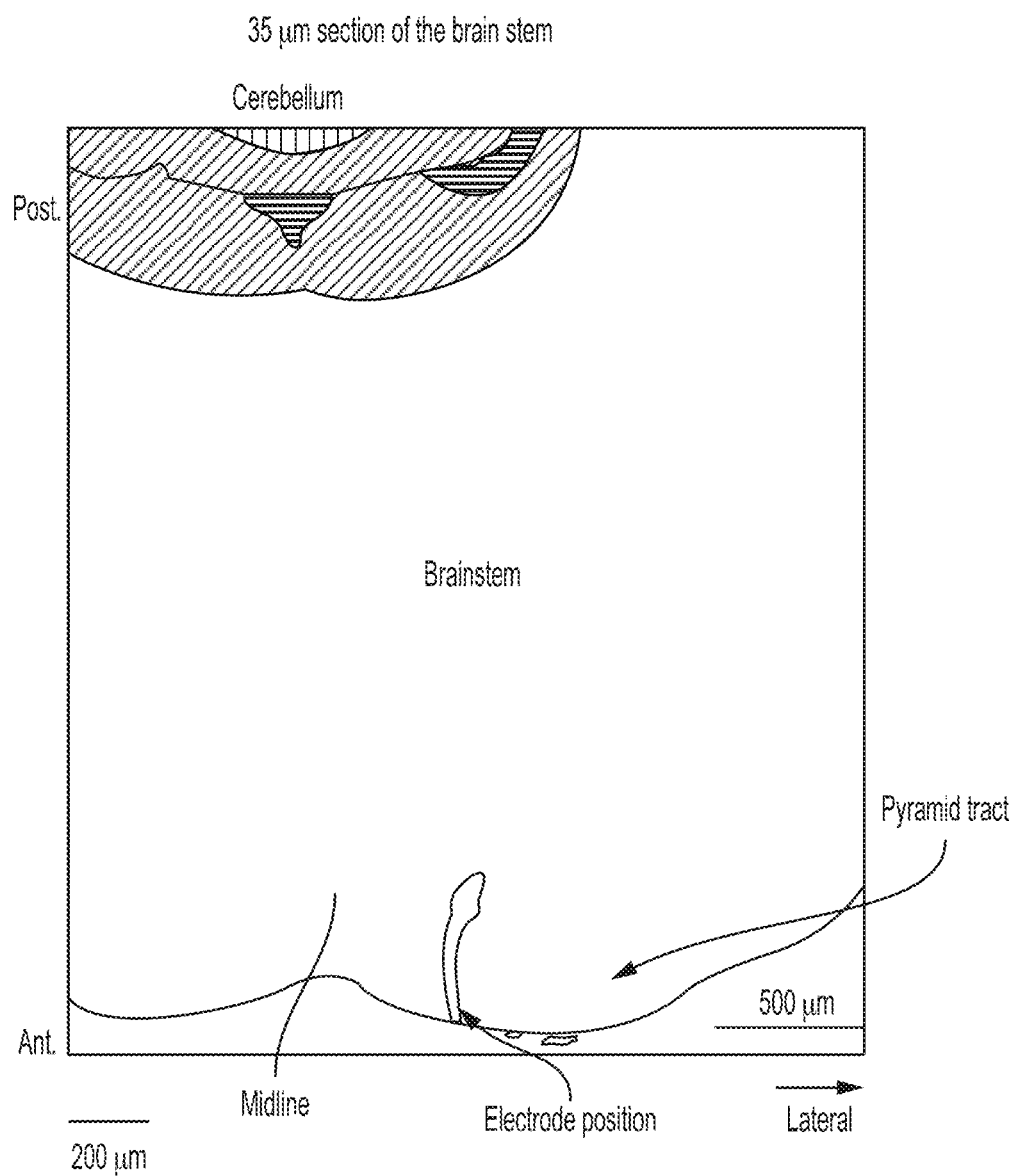
FIG. 18 illustrates example placement of electrodes along the pyramid tract, according to an example embodiment, according to an example embodiment.

During the experiments, measurements were performed of SCS evoked activity in the Gracilis nucleus and for antidromic evoked volleys in the Pyramid using the recording microelectrodes. FIG. 18 illustrates example placement of electrodes along the pyramid tract. Stimulation intensity was increased or decreased in increments as shown in Table 1 below.

TABLE 1

| Intensity Range | Increments |
| --- | --- |
| 10-50 mV | 10 mV |
| 50-400 mV | 25 mV |
| 400-900 mV | 50 mV |
| 900-1200 mV | 100 mV |
| ≥1200 mV | 250 |

A lowest stimulation intensity eliciting a clear response was considered a threshold for evoking activity in the Gacilis nucleus and the Pyramid.

During the experiments, each sampled data file is an average of about 400 single recording experiments. Latency of the Pyramid tract responses which were used in the analysis (16-19 m/s) were consistent with those observed in the literature (See, e.g., Mediratta and Nicoll J *Physiol.* 1983 Mar.; 336:545-6 1; Stewart et al. *Brain Res.* 1990 Feb. 5; 508(2):34 1-4; and Chapman and Yeomans *Neuroscience* 1994, 59(3):699-711).

The Experiments showed that thresholds for activation of both the Gracile nucleus and the Pyramid were significantly lower when using 100+105 Hz interferential current stimulation than using conventional 100+100 Hz stimulation in either the parallel or crossed configuration.

Figures 19A, 19B, 19C:
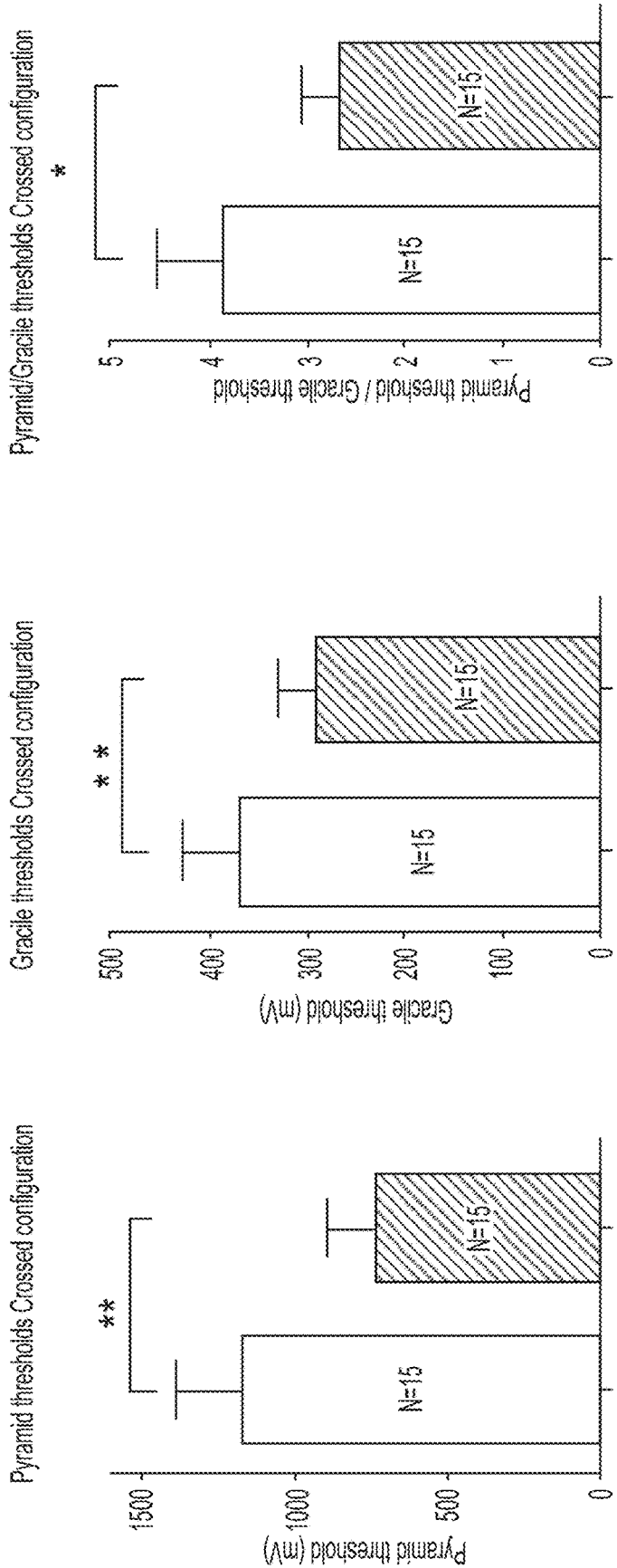
FIGS. 19A-C illustrate comparisons of threshold data after 2000+2000 Hz versus 2000+2100 Hz stimulation using a crossed electrode configuration, according to an example embodiment.
Figures 20A, 20B, 20C:
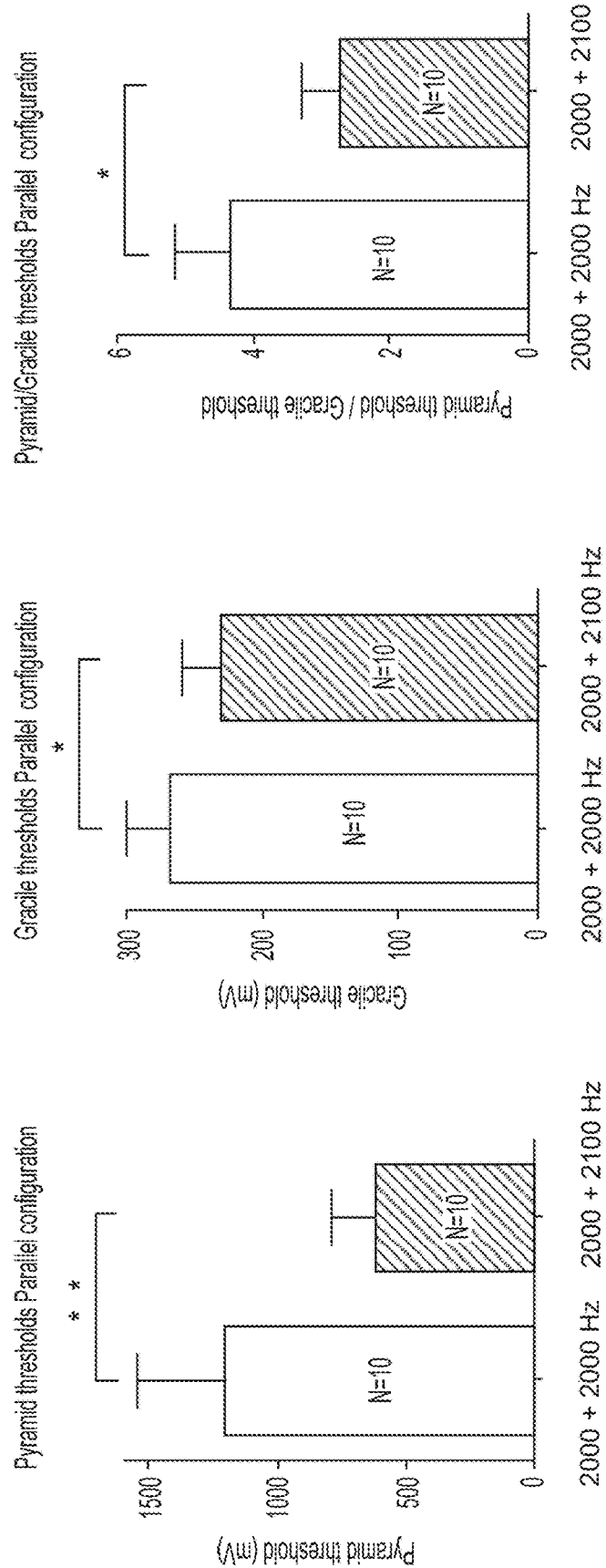
FIGS. 20A-C illustrate comparisons of threshold data after 2000+2000 Hz versus 2000+2100 Hz stimulation using a parallel electrode configuration, according to an example embodiment.

FIGS. 19A-C illustrate comparisons of threshold data after 100+100 Hz versus 100+105 Hz stimulation using a crossed electrode configuration. Results after Wilcoxon signed rank significance test is shown. N equals the number of animals used, e.g., 15. FIGS. 20A-C illustrate comparisons of threshold data after 100+100 Hz versus 100+105 Hz stimulation using a parallel electrode configuration. Results after Wilcoxon signed rank significance test is shown. N equals the number of animals used, e.g., 10.

As seen in FIGS. 19 and 20, for Pyramid activation, conventional stimulation (left side of bar graphs) required about 1200 mV (in the parallel and cross configuration); by comparison, interferential stimulation (right side of bar graphs) required only about 700 mV in the cross configuration or about 600 mV in the parallel configuration. For Gracile activation, conventional stimulation required about 375 mV in the cross configuration or about 275 mV in the parallel configuration; by comparison, interferential stimulation required only about 290 mV in the cross configuration or about 225 mV in the parallel configuration.

To yield a better understanding of the efficacy of the stimulation, a ratio of the threshold for Pyramid tract activation versus the threshold for Gracile nucleus activation was graphed. The lower the ratio, the more efficient stimulation to the deep Pyramidal tract in relation to the Gracile nucleus tract (which is more superficial). The graphs illustrate ratios of about 4 using the conventional stimulation as compared to only about 2 using the interferential stimulation. Thus, interferential stimulation achieves better penetration to the deeper Pyramidal tract than conventional stimulation.

The experimental results demonstrate that interference stimulation with 100+105 Hz (2000 Hz+2100 Hz) is more effective than 100+100 Hz conventional stimulation in activating the pathways studied, both from a threshold and depth-penetration perspective. This indicates that the formation of an interference pattern or beat frequency provided a lower threshold and better penetration.

Applying stimulation using conventional surface electrodes does not enable deep penetration of the pyramid tract. Electricity follows a path of least resistance, and applying stimulation on the surface of the skin using surface electrodes does not allow for stimulation through the vertebrae. Bone is an insulator and has a conductivity of 0.06 s/m, while skin has a conductivity of 0.436 s/m. To achieve stimulation levels of the pyramid tract as seen in the experiments using surface stimulation, stimulation would need to be applied at a voltage level so high that it would result in tissue damage and pain.

Table 2 below summarizes the results of the experiments. It shows the approximate voltage levels required to activate the Gracile nucleus and the Pyramid tract in the spinal cord using an interferential implantable electrode configuration and a conventional implantable electrode configuration. The results of the experiments demonstrate that the activation thresholds in the Gracile nucleus and the Pyramid tract in the dorsal column are significantly lower when using 100+105 Hz interferential current stimulation than when using conventional 100+100 Hz stimulation. Furthermore, the same kind of results were obtained regardless of whether the conventional stimulation was performed in the parallel or crossed configuration. More specifically, the activation thresholds for the deep Pyramid tract were reduced by about 50% using the interferential current stimulation in either the parallel or crossed configuration. Moreover, the activation threshold for the Gracile nucleus was reduced by about 20% using interferential current stimulation in either the parallel or cross configuration.

TABLE 2

| | Results using Interferential Implantable Electrode Configuration | | Results using Conventional Implantable Electrode Configuration | | Results using Interferential Surface Electrode Configuration |
|---|---|---|---|---|---|
| | Parallel Configuration | Crossed Configuration | Parallel Configuration | Crossed Configuration | |
| Pyramid Activation Threshold | 600 mV | 700 mV | 1200 mV | 1200 mV | >>1200 mV |
| Gracile Activation Threshold | 225 mV | 290 mV | 275 mV | 375 mV | >>1200 mV |

As shown in Table 2, the interferential implantable electrode configuration achieves activation of the Gracile nucleus and Pyramid in the spinal cord at much lower voltage levels than are required with a conventional implantable electrode configuration, thereby providing effective pain relief while minimizing the risk of stimulation of the dorsal root ganglia, which could lead to chest and thoracic pain.

Table 2 also includes estimates for approximate voltages levels that would be required using an interferential surface electrode configuration. For example, using the experimental results, it can be calculated that to achieve stimulation of the Gracile nucleus and the Pyramid in the spinal cord using an interferential surface electrode configuration, voltage levels would be required that are much greater than 1200 mV, and are more on the order of 100's of volts, for example. In any event, the voltage levels are so high that they are physiologically unsafe. In any event, it is not true that with any application of interferential therapy, electrodes can simply be implanted, and the therapy can be scaled down so that intensity values of the current would be within acceptable levels (that do not cause pain) while still providing effective therapy to the patient. In contrast, implantable stimulators are generally used when other physical therapy options have been unsuccessful.

Thus, neuronal tracts that lie beneath the surface of the Dorsal Columns (i.e., >0.5 mm) can be successfully stimulated using an interferential pattern of electrical fields. The interferential capability allows for more precise neurostimulation of the adjacent Dorsal root Entry Zone at one level, with complementary stimulation of the corresponding neuronal tracts deep within the Dorsal Columns at a different level (depending on the ultimate lead design). Other applications include highly precise neurostimulation of the nerve roots and the Dorsal Root Ganglia themselves, all from an intraspinal, epidural location. This ability for control of neuronal stimulation from a three-dimensional perspective is potentially of considerable importance in advancing the clinical capabilities of neurostimulation within the spinal canal, and beyond.

It should be emphasized that the above-described embodiments of the present disclosure are merely possible examples of implementations set forth for a clear understanding. Many variations and modifications may be made to the above-described embodiment(s) without departing substantially from the principles of the disclosure. All such modifications and variations are intended to be included herein within the scope of this disclosure and protected by the following claims.

What is claimed is:

1. A method for spinal cord stimulation using electrical stimulation of a spinal cord, for providing positive regulation of multiple symptoms other than pain, the method comprising:
   positioning a first pair of implantable electrodes to a dura matter in an epidural space proximate to a subject's spinal cord at predetermined locations;
   positioning a second pair of implantable electrodes to the dura matter in the epidural space proximate to the subject's spinal cord at predetermined locations; and
   transmitting signals of first and second frequencies through the first and second pairs of implantable electrodes respectively, so that the signals of the first and second frequencies interfere with each other to produce at least one beat signal proximate to the subject's spinal cord, wherein the at least one beat signal has a frequency within a range of 10,000 Hz to about 15,000 Hz.

2. The method of claim 1, wherein the method is used for providing regulation of cardiovascular functions.

3. The method of claim 1, wherein the method is used for providing regulation of neuroendocrine functions.

4. The method of claim 1, wherein the method is used for providing regulation of respiratory functions.

5. The method of claim 1, wherein the method is used for providing regulation of emotional functions.

6. The method of claim 1, further comprising overcoming capacitive resistance of interfaces between different tissue types and tissue membranes to allow passage of sub-threshold and threshold current to deeper layers of the spinal cord.

7. The method of claim 1, further comprising producing at least one beat signal proximate to the subject's spinal cord, and avoiding the at least one beat signal remaining in and shunting through cerebrospinal fluid proximate the subject's dorsal column through directional control.

8. The method of claim 1, further comprising producing the at least one beat signal into the subject's tissue proximate to one or more of a Gracile nucleus and a Pyramid tract of the spinal cord through directional control of the at least one beat signal for activating the Gracile nucleus and the Pyramid tract.

9. The method of claim 1, further comprising producing the at least one beat signal deep into the subject's tissue proximate to one or more of an ascending pathway from the spinal cord to the subject's thalamus including one or more of spinothalamic, spinoreticular, spinomesencephalic, cerviocothalamic and spinohypothalamic tracts.

10. The method of claim 1, wherein positioning the first pair of implantable electrodes and positioning the second pair of implantable electrodes comprises:
    positioning the first pair of implantable electrodes and the second pair of implantable electrodes in a crossing configuration such that a first circuit created between the first pair of implantable electrodes crosses a second circuit created between the second pair of implantable electrodes.

11. The method of claim 1, wherein positioning the first pair of implantable electrodes and positioning the second pair of implantable electrodes comprises:
    positioning the first pair of implantable electrodes and the second pair of implantable electrodes in a parallel configuration such that a first circuit created between the first pair of implantable electrodes is parallel to a second circuit created between the second pair of implantable electrodes.

12. The method of claim 11, wherein the first circuit and the second circuit generate a first field and a second field, and wherein positioning the first pair of implantable electrodes and positioning the second pair of implantable electrodes comprises:
    positioning the first pair of implantable electrodes and positioning the second pair of implantable electrodes such that the first field and the second field overlap to produce the at least one beat signal.

13. The method of claim 12, further comprising biasing the first pair of implantable electrodes and the second pair of implantable electrodes to cause alignment of the first field and the second field in a target region of concentration, and wherein the first pair of implantable electrodes and the second pair of implantable electrodes are proximal to each other to form an area of overlap of the first field and the second field.

14. The method of claim 12, further comprising biasing the first pair of implantable electrodes and the second pair of implantable electrodes to cause the first field and the second field to be unaligned for an untargeted region of concentration.

15. A method for spinal cord stimulation using electrical stimulation of a spinal cord, for providing positive regulation of multiple symptoms other than pain, the method comprising:
    positioning a first pair of implantable electrodes to a dura matter in an epidural space proximate to a subject's spinal cord at predetermined locations such that a first circuit is created between the first pair of implantable electrodes;
    positioning a second pair of implantable electrodes to the dura matter in the epidural space proximate to the subject's spinal cord at predetermined locations such that a second circuit is created between the second pair of implantable electrodes, wherein the first pair of implantable electrodes and the second pair of implantable electrodes are positioned in a parallel configuration such that a first electrode and a second electrode of one pair of implantable electrodes are aligned vertically along a longitudinal axis of the spinal cord to form the first circuit and a first electrode and a second electrode of the other pair of implantable electrodes are aligned vertically along the longitudinal axis of the spinal cord to form the second circuit and the first circuit is parallel to the second circuit; and
    transmitting a signal of a first frequency through the first circuit and a signal of a second frequency through the second circuit, so that the signal of the first frequency and the signal of the second frequency interfere with each other to produce at least one beat signal proximate to the subject's spinal cord, wherein the at least one beat signal has a frequency within a range of 10,000 Hz to about 15,000 Hz.

16. The method of claim 15, wherein the method is used for providing regulation of cardiovascular functions.

17. The method of claim 15, wherein the method is used for providing regulation of neuroendocrine functions.

18. The method of claim 15, wherein the method is used for providing regulation of respiratory functions.

19. The method of claim 15, wherein the method is used for providing regulation of emotional functions.

20. The method of claim 15, further comprising producing the at least one beat signal into the subject's tissue proximate to one or more of a Gracile nucleus and a Pyramid tract of the spinal cord through directional control of the at least one beat signal for activating the Gracile nucleus and the Pyramid tract.

* * * * *